United States Patent
Ford et al.

(10) Patent No.: US 10,559,754 B2
(45) Date of Patent: *Feb. 11, 2020

(54) ORGANIC SEMICONDUCTOR SOLUTION BLENDS FOR SWITCHING AMBIPOLAR TRANSPORT TO N-TYPE TRANSPORT

(71) Applicant: The Regents of the University of California, Oakland, CA (US)

(72) Inventors: Michael J. Ford, Santa Barbara, CA (US); Hengbin Wang, Santa Barbara, CA (US); Guillermo C. Bazan, Santa Barbara, CA (US)

(73) Assignee: THE REGENTS OF THE UNIVERSITY OF CALIFORNIA, Oakland, CA (US)

(*) Notice: Subject to any disclaimer, the term of this patent is extended or adjusted under 35 U.S.C. 154(b) by 0 days.

This patent is subject to a terminal disclaimer.

(21) Appl. No.: 15/599,816

(22) Filed: May 19, 2017

(65) Prior Publication Data

US 2017/0338415 A1  Nov. 23, 2017

Related U.S. Application Data

(60) Provisional application No. 62/338,866, filed on May 19, 2016.

(51) Int. Cl.
*H01L 51/00* (2006.01)
*C07D 521/00* (2006.01)
*H01L 51/05* (2006.01)

(52) U.S. Cl.
CPC ........ *H01L 51/0035* (2013.01); *C07D 521/00* (2013.01); *H01L 51/0077* (2013.01); *H01L 51/0545* (2013.01)

(58) Field of Classification Search
CPC .......... H01L 51/0035; H01L 51/0034
See application file for complete search history.

(56) References Cited

U.S. PATENT DOCUMENTS

2005/0069727 A1* 3/2005 Gupta ................. H01L 51/0034
428/690
2013/0161599 A1* 6/2013 Katz ................... H01L 51/0558
257/40

(Continued)

FOREIGN PATENT DOCUMENTS

WO  WO 2014/039847  * 3/2014

OTHER PUBLICATIONS

Qiu, Organic Thin-Film Transistors Based on Blends of Poly(3-hexylthiophene) and Polystyrene with a Solubility-Induced Low Percolation, 2009, Chem. Matter, 21, 4380-4386. (Year: 2009).*

(Continued)

*Primary Examiner* — Mounir S Amer
(74) *Attorney, Agent, or Firm* — Gates & Cooper LLP

(57) ABSTRACT

The present disclosure describes additives that attenuate a specific transport channel in ambipolar semiconductors to achieve unipolar characteristics. Carrier selective traps are included in the ambipolar semiconductors and are chosen on the basis of energetic preferences for holes or electrons and the relative positions of the molecular orbital energies of host polymer and the dopants. In one embodiment, a composition of matter useful as a current transport region in an organic semiconductor device comprises a semiconducting polymer; and means for accepting holes (e.g., a hole trapping compound) injected into the current transport region so as to impede conduction of the holes in the semiconducting polymer. This simple solution-processable method can improve the on and off current ratios ($I_{ON}/I_{OFF}$) of OFETs by up to three orders of magnitude. Moreover, the treatment yields tailored blends that can be used to fabricate complementary inverters with excellent gain and low-power characteristics.

23 Claims, 24 Drawing Sheets

(56) References Cited

U.S. PATENT DOCUMENTS

2013/0214249 A1* 8/2013 Pan ................ H01L 51/5012 257/13
2015/0214486 A1* 7/2015 Tseng ............... H01L 51/0012 257/40

OTHER PUBLICATIONS

Ying, L., et al., "Regioregular Pyridal[2,1,3]thiadiazole π-Conjugated Copolymers", Journal of American Chemical Society, ACS Publications, 2011, pp. 18538-18541, vol. 133.

Tseng, H-R., et al., "High Mobility Field Effect Transistors Based on Macroscopically Oriented Regioregular Copolymers", ACS Publications, American Chemical Society—Nano Letters, 2012, pp. 6353-6357, vol. 12.

Tseng, H-R., et al., "High-Mobility Field-Effect Transistors Fabricated with Macroscopic Aligned Semiconducting Polymers", Advanced Materials, 2014, pp. 2993-2998, vol. 26.

Ford, M.J., et al., "High Mobility Organic Field-Effect Transistors from Majority Insulator Blends", ACS Publications, American Chemical Society—Chemistry of Materials, 2016, pp. 1256-1260, vol. 28.

Sirringhaus, H., "25th Anniversary Article: Organic Field-Effect Transistors: The Path Beyond Amorphous Silicon", Advanced Materials, 2014, pp. 1319-1335, vol. 26.

Bartelt, J.A., et al., "The Importance of Fullerene Percolation in the MixedRegions of Polymer-Fullerene Bulk Heterojunction Solar Cells", Advanced Energy Materials, 2013, pp. 364-374, vol. 3.

Köhler, A., "Organic Semiconductors—No more breaks for electrons", Nature Materials, Oct. 2012, pp. 836-837, vol. 11.

Facchetti, A., "Organic Semiconductors—Made to order", Nature Materials, Jul. 2013, pp. 598-600, vol. 12.

Ford, M.J., et al., "Fullerene Additives Convert Ambipolar Transport to p-Type Transport while Improving the Operational Stability of Organic Thin Film Transistors", Advanced Functional Materials, 2016, pp. 4472-4480, vol. 26.

Luo, C., et al., "General Strategy for Self-Assembly of Highly Oriented Nanocrystalline Semiconducting Polymers with High Mobility", ACS Publications, American Chemical Society, Nano Letters, 2014, pp. 2764-2771, vol. 14.

Ford, M.J., et al., "Carrier-Selective Traps: A New Approach for Fabricating Circuit Elements with Ambipolar Organic Semiconductors", Advanced Electronic Materials, 2017, pp. 1-6, vol. 3, 1600537.

* cited by examiner e⁻ trap      ambipolar semiconductor      h⁺ trap

PC$_{61}$BM      DT-PDPP2T-TT      CuBP

ORGANIC SEMICONDUCTOR SOLUTION BLENDS FOR SWITCHING AMBIPOLAR TRANSPORT TO N-TYPE TRANSPORT

CROSS REFERENCE TO RELATED APPLICATIONS

This application claims the benefit under 35 U.S.C. Section 119(e) of and commonly-assigned U.S. Provisional Patent Application No. 62/338,866, filed May 19, 2016, by Michael J. Ford, Hengbin Wang, and Guillermo Bazan, entitled "ORGANIC SEMICONDUCTOR SOLUTION BLENDS FOR SWITCHING AMBIPOLAR TRANSPORT TO N-TYPE TRANSPORT";

which application is incorporated by reference herein.

This application is related to the following co-pending and commonly-assigned U.S. patent applications:

U.S. Utility patent application Ser. No. 15/400,579, filed Jan. 6, 2017, by Michael J. Ford and Guillermo Bazan, entitled "STABLE ORGANIC FIELD-EFFECT TRANSISTORS BY INCORPORATING AN ELECTRON-ACCEPTING MOLECULE", which application claims the benefit under 35 U.S.C. Section 119(e) of U.S. Provisional Patent Application No. 62/276,145, filed Jan. 7, 2016, by Michael J. Ford and Guillermo Bazan, entitled "STABLE ORGANIC FIELD-EFFECT TRANSISTORS BY INCORPORATING AN ELECTRON-ACCEPTING MOLECULE";

U.S. Utility patent application Ser. No. 15/496,826, filed Apr. 25, 2017, by Guillermo Bazan and Ming Wang, entitled "NOVEL WEAK DONOR-ACCEPTOR CONJUGATED COPOLYMERS FOR FIELD-EFFECT TRANSISTOR APPLICATIONS", which application claims the benefit under 35 U.S.C. Section 119(e) of U.S. Provisional Patent Application No. 62/327,311, filed Apr. 25, 2016, by Guillermo C. Bazan and Ming Wang, entitled "NOVEL WEAK DONOR-ACCEPTOR CONJUGATED COPOLYMERS FOR FIELD-EFFECT TRANSISTOR APPLICATIONS"; and U.S. Provisional Patent Application No. 62/489,303, filed Apr. 24, 2017, by Guillermo C. Bazan and Ming Wang, entitled "LINEAR CONJUGATED POLYMER BACKBONES IMPROVE THE ANISOTROPIC MORPHOLOGY IN NANOGROOVE ASSISTED ALIGNMENT ORGANIC FIELD-EFFECT TRANSISTOR APPLICATIONS", U.S. Provisional Patent Application No. 62/327,311, filed Apr. 25, 2016, by Guillermo Bazan and Ming Wang, entitled "NOVEL WEAK DONOR-ACCEPTOR CONJUGATED COPOLYMERS FOR FIELD-EFFECT TRANSISTOR APPLICATIONS";

U.S. Utility patent application Ser. No. 15/349,920, filed Nov. 11, 2016, by Ming Wang and Guillermo Bazan, entitled "FLUORINE SUBSTITUTION INFLUENCE ON BENZO[2,1,3]THIODIAZOLE BASED POLYMERS FOR FIELD-EFFECT TRANSISTOR APPLICATIONS", which application claims the benefit under 35 U.S.C. Section 119(e) of U.S. Provisional Patent Application No. 62/253,975, filed Nov. 11, 2015, by Ming Wang and Guillermo Bazan, entitled "FLUORINE SUBSTITUTION INFLUENCE ON BENZO[2,1,3]THIODIAZOLE BASED POLYMERS FOR FIELD-EFFECT TRANSISTOR APPLICATIONS";

U.S. Utility patent application Ser. No. 15/349,920, filed Nov. 11, 2016, by Byoung Hoon Lee, Ben B. Y. Hsu, Chan Luo, Ming Wang, Guillermo Bazan, and Alan J. Heeger, entitled "SEMICONDUCTING POLYMERS WITH MOBILITY APPROACHING ONE HUNDRED SQUARE CENTIMETERS PER VOLT PER SECOND", which application claims the benefit under 35 U.S.C. Section 119(e) of U.S. Provisional Patent Application No. 62/263,058, filed Dec. 4, 2015, by Byoung Hoon Lee, Ben B. Y. Hsu, Chan Luo, Ming Wang, Guillermo Bazan, and Alan J. Heeger, entitled "SEMICONDUCTING POLYMERS WITH MOBILITY APPROACHING ONE HUNDRED SQUARE CENTIMETERS PER VOLT PER SECOND";

U.S. Utility patent application Ser. No. 15/256,160, filed Sep. 2, 2016, by Byoung Hoon Lee and Alan J. Heeger, entitled "DOPING-INDUCED CARRIER DENSITY MODULATION IN POLYMER FIELD-EFFECT TRANSISTORS", which application claims the benefit under 35 U.S.C. Section 119(e) of commonly-assigned U.S. Provisional Patent Application No. 62/214,076, filed Sep. 3, 2015, by Byoung Hoon Lee and Alan J. Heeger, entitled "DOPING-INDUCED CARRIER DENSITY MODULATION IN POLYMER FIELD-EFFECT TRANSISTORS";

U.S. Utility patent application Ser. No. 15/241,949 filed Aug. 19, 2016, by Michael Ford and Guillermo Bazan, entitled "HIGH MOBILITY POLYMER ORGANIC FIELD-EFFECT TRANSISTORS BY BLADE-COATING SEMICONDUCTOR: INSULATOR BLEND SOLUTIONS", which application claims the benefit under 35 U.S.C. Section 119(e) of U.S. Provisional Patent Application No. 62/207,707, filed Aug. 20, 2015, by Michael Ford and Guillermo Bazan, entitled "HIGH MOBILITY POLYMER ORGANIC FIELD-EFFECT TRANSISTORS BY BLADE-COATING SEMICONDUCTOR: INSULATOR BLEND SOLUTIONS"; and U.S. Provisional Patent Application No. 62/262,025, filed Dec. 2, 2015, by Michael Ford and Guillermo Bazan, entitled "HIGH MOBILITY POLYMER ORGANIC FIELD-EFFECT TRANSISTORS BY BLADE-COATING SEMICONDUCTOR: INSULATOR BLEND SOLUTIONS";

U.S. Utility application Ser. No. 15/213,029 filed on Jul. 18, 2016 by Byoung Hoon Lee and Alan J. Heeger, entitled "FLEXIBLE ORGANIC TRANSISTORS WITH CONTROLLED NANOMORPHOLOGY", which application claims the benefit under 35 U.S.C. Section 119(e) of U.S. Utility U.S. Provisional Application Ser. No. 62/193,909 filed on Jul. 17, 2015 by Byoung Hoon Lee and Alan J. Heeger, entitled "FLEXIBLE ORGANIC TRANSISTORS WITH CONTROLLED NANOMORPHOLOGY";

U.S. Utility patent application Ser. No. 15/058,994, filed Mar. 2, 2016, by Shrayesh N. Patel, Edward J. Kramer, Michael L. Chabinyc, Chan Luo and Alan J. Heeger, entitled "BLADE COATING ON NANOGROOVED SUBSTRATES YIELDING ALIGNED THIN FILMS OF HIGH MOBILITY SEMICONDUCTING POLYMERS", which Application claims the benefit under 35 U.S.C. Section 119(e) of U.S. Provisional Patent Application No. 62/127,116, filed Mar. 2, 2015, by Shrayesh N. Patel, Edward J. Kramer, Michael L. Chabinyc, Chan Luo and Alan J. Heeger, entitled "BLADE COATING ON NANOGROOVED SUBSTRATES YIELDING ALIGNED THIN FILMS OF HIGH MOBILITY SEMICONDUCTING POLYMERS";

U.S. Utility patent application Ser. No. 14/585,653, filed on Dec. 30, 2014, by Chan Luo and Alan Heeger, entitled "HIGH MOBILITY POLYMER THIN FILM TRANSISTORS WITH CAPILLARITY MEDIATED SELF-ASSEMBLY", which application claims the benefit under 35 U.S.C. Section 119(e) of U.S. Provisional Patent Application Ser. No. 61/923,452, filed on Jan. 3, 2014, entitled "HIGH MOBILITY POLYMER THIN FILM TRANSISTORS WITH CAPILLARITY MEDIATED SELF-ASSEMBLY";

U.S. Utility patent application Ser. No. 14/426,467, filed on Mar. 6, 2015, by Hsing-Rong Tseng, Lei Ying, Ben B. Y. Hsu, Christopher J. Takacs, and Guillermo C. Bazan, entitled "FIELD-EFFECT TRANSISTORS BASED ON MACROSCOPICALLY ORIENTED POLYMERS"; which application claims the benefit under 35 U.S.C. § 365 of PCT International patent application serial no. PCT/US13/058546 filed Sep. 6, 2013, which application claims the benefit under 35 U.S.C. Section 119(e) of U.S. Provisional Patent Application Ser. Nos. 61/698,065, filed on Sep. 7, 2012, and 61/863,255, filed on Aug. 7, 2013, entitled "FIELD-EFFECT TRANSISTORS BASED ON MACROSCOPICALLY ORIENTED POLYMERS"; and U.S. Utility patent application Ser. No. 13/526,371, filed on Jun. 18, 2012, by G. Bazan, L. Ying, B. Hsu, W. Wen, H-R Tseng, and G. Welch entitled "REGIOREGULAR PYRIDAL[2,1,3]THIADIAZOLE PI-CONJUGATED COPOLYMERS FOR ORGANIC SEMICONDUCTORS", which application claims priority under 35 U.S.C. § 119(e) to U.S. Provisional Patent Application Ser. No. 61/498,390, filed on Jun. 17, 2011, by G. Bazan, L. Ying, B. Hsu, and G. Welch entitled "REGIOREGULAR CONSTRUCTIONS FOR THE SYNTHESIS OF THIADIAZOLO (3,4) PYRIDINE CONTAINING NARROW BAND GAP CONJUGATED POLYMERS" and U.S. Provisional Patent Application Ser. No. 61/645,970, filed on May 11, 2012, by G. Bazan, L. Ying, and Wen, entitled "REGIOREGULAR PYRIDAL[2,1,3]THIADIAZOLE PI-CONJUGATED COPOLYMERS FOR ORGANIC SEMICONDUCTORS";

all of which applications are incorporated by reference herein.

BACKGROUND OF THE INVENTION

1. Field of the Invention

This invention relates to methods and compositions for reducing hole current in semiconducting polymers.

2. Description of the Related Art (Note: This application references a number of different references as indicated throughout the specification by one or more reference numbers in bracketed superscripts, e.g.) .,[x]. A list of these different references ordered according to these reference numbers can be found below in the section entitled "References." Each of these references is incorporated by reference herein.)

Electronic devices driven by polymeric semiconductors are compatible with large-area production on flexible substrates and low-temperature solution processing. Example polymer structures utilize an alternating donor-acceptor design strategy, where an electron rich moiety is the donor (D) and an electron deficient moiety is the acceptor (A) in each repeat unit.

However, in the reported D-A type high mobility polymers, strong acceptors (DPP, IDG, BT, and their derivatives) usually induce an ambipolar charge transporting effect wherein the polymer can transport positive and negative charge carriers. This is useful but presents a problem in real applications; e.g., since an Organic Field Effect Transistor (OFET) comprising an ambipolar polymer injects positive charge carriers at a negative gate voltage and negative charge carriers at a positive gate voltage, so that the device is never truly "off". Improvement of the on/off ratio of the current would improve the potential performance in circuits using ambipolar polymers. The present invention satisfies this need.

SUMMARY OF THE INVENTION

The present disclosure describes intentionally introducing extrinsic charge-selective traps into a conjugated polymer capable of ambipolar transport in order to attenuate p-type or n-type transport.

One embodiment of the invention comprises a composition of matter or composite including one or more donor-acceptor semiconducting copolymers combined with means for trapping holes (e.g., one or more hole trapping compounds) so that the means for trapping holes reduces or suppresses hole current in the one or more donor-acceptor copolymers.

To better illustrate the composition of matter disclosed herein, a non-limiting list of examples is provided here:

In Example 1, the composition of matter comprises a solution wherein a total weight percentage (wt. %) of the hole trapping compound(s) in the solution is in a range of 0.005-50 wt. % (e.g., 0.005-10 wt. %) based on a total weight of the solution.

In Example 2, the composition of matter is cast from a solution, wherein a total weight ($W_{CP}$) of the donor-acceptor copolymer(s) added in the solution and a total weight $W_{HT}$ of the hole trapping compound(s) added in the solution are such that $[W_{CP}/(W_{CP}+W_{HT})]\times 100$ is in a range of 5%-99%.

In Example 3, the hole trapping compounds of one or any combination of Examples 1-2 each comprise at least one compound selected from Tetrathiafulvalene (TTF), a derivative of TTF, 1H-benzoimidazole (DMBI), a derivative of DMBI, Decamethylcobaltocene (DMC), a derivative of DMC, tetrabenzoporphyrin (BP or TBP), a derivative of BP, copper tetrabenzoporphyrin (CuBP), a derivative of CuBP, bicyclo[2,2,2]-octadiene-fused porphyrins, tetraethano-tetrabenzoporphyrin (CuCP, or CuBP precursor), a derivative of tetraethano-tetrabenzoporphyrin, copper tetraethano-tetrabenzoporphyrin, a derivative of copper tetraethano-tetrabenzoporphyrin, Spiro-MeOTAD, and a derivative of Spiro-MeOTAD.

In Example 4, the donor-acceptor copolymers of one or any combination of Examples 1-3 each comprise a main chain section having a repeat unit that comprises a donor and an acceptor, wherein the copolymer is regioregular or non-regioregular.

In Example 5, the acceptor in the copolymer of one or any combination of Examples 1-4 comprises a pyridine of the structure:

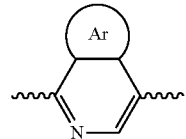

wherein Ar is a substituted or non-substituted aromatic functional group or Ar is nothing and the valence of the pyridine ring is completed with hydrogen; and the pyridine is regioregularly arranged along the conjugated main chain section.

In Example 6, the acceptor in the copolymer of one or any combination of Examples 1-4 comprises a fluorophenyl or fluorophenylene.

In Example 7, the donor in the copolymer of one or any combination of Examples 1-6 comprises a dithiophene of the structure:

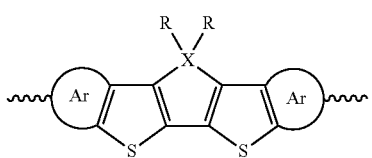

wherein each R is independently hydrogen or a substituted or non-substituted alkyl, aryl, or alkoxy chain; and X is C, Si, Ge, N or P; n Example 8, each of the donor-acceptor copolymers of one or any combination of Examples 1-5 or 7 are poly[4-(4,4-dihexadecyl-4H-cyclopenta[1,2-b:5,4-b']dithiophen-2yl)-alt-[1,2,5]thiadiazolo[3,4-c]pyridine] (PCDTPT).

In Example 9, each of the donor-acceptor copolymers of one or any combination of Examples 1-4 or 6-7 are poly[5-fluoro-[2,1,3]benzothiadiazole-4,7-diyl(4,4-dihexadecyl-4H-cyclopenta[2,1-b:3,4-b']dithiophene-2,6-diyl)-5-fluoro-[2,1,3]benzothiadiazole-7,4-diyl(4,4-dihexadecyl-4H-cyclopenta[2,1-b:3,4-b']dithiophene-2,6-diyl)] (PCDTFBT), or In Example 10, each of the donor-acceptor copolymers of one or any combination of Examples 1-4 are copolymers containing diketopyrrolopyrrole (DPP) repeating units, examples of DPP containing polymers include, but are not limited to DT-PDPP2T-TT and those listed in FIGS. 11a-11l of U.S. Utility patent application Ser. No. 15/400,579 cross-referenced above (entitled "STABLE ORGANIC FIELD-EFFECT TRANSISTORS BY INCORPORATING AN ELECTRON-ACCEPTING MOLECULE".

In Example 11, introduction of an effective hole trapping compound of one or any combination of Examples 1-10 switches ambipolar transport (in an ambipolar semiconducting donor-acceptor copolymer) to electron-only (n-type) transport and/or such that hole current is reduced relative to electron current in the semiconducting donor-acceptor copolymer.

In Example 12, the composition of matter of one or any combination of Examples 1-11 has a first region including the donor-acceptor copolymers combined with the hole trapping compounds; and a second region attached to the first region and including additional donor-acceptor copolymers combined with electron acceptor compounds, the electron acceptor compounds accepting electrons and reducing electron current in the additional donor-acceptor copolymer.

In Example 13, the subject matter of Example 12 further includes the donor-acceptor copolymers in the first region and the additional donor-acceptor copolymers in the second region both comprising a backbone including substantially the same repeat unit.

In Example 14, the donor-acceptor copolymers and the hole trapping compounds of one or any combination of Examples 1-13 are disposed in a film, wherein the donor-acceptor copolymers and the hole trapping compounds are phase separated, and the main chain axes of a plurality of the donor-acceptor copolymers are interconnected.

In Example 15, the composition of matter of one or any combination of Examples 1-14 is disposed in an OFET, the OFET comprising a source contact to the donor-acceptor copolymers; a drain contact to the donor-acceptor copolymers; a gate contact; and a dielectric between the donor-acceptor copolymers and the gate contact.

In Example 16, the OFET of Example 15 is such that a hole current between the source and the drain contact is reduced by at least a factor of 100, when the OFET is biased in the off state, with at most a factor of 10 reduction in electron current between the source and the drain contacts, when the OFET is biased in the on state, as compared to the OFET comprising a film comprising the pristine donor-acceptor copolymers without the hole trapping compounds.

In Example 17, the OFET of one or any combination of Examples 15-16 is connected to an additional OFET, the additional OFET comprising additional donor-acceptor copolymers combined with electron acceptor compounds, the electron acceptor compounds accepting electrons and reducing electron current in the additional donor-acceptor copolymers.

In Example 18, the OFETs of one or any combination of Examples 15-17 further includes a weight and composition of the hole trapping compounds, a weight and composition of the donor-acceptor copolymers, and optionally a weight of and composition of the electron acceptor compounds, such that each of the OFETs have a mobility in a saturation regime of at least 1 cm$^2$ V$^{-1}$s$^{-1}$.

In Example 19, the OFETs of one or any combination of Examples 15-18 further include a weight and composition of the hole trapping compounds, a weight and composition of the donor-acceptor copolymers, and optionally a weight of and composition of the electron acceptor compounds, such that the OFETs have an ON/OFF ratio of at least 1000.

In Example 20, the OFETs of one or any combination of Examples 17-19 are disposed/connected so as to form a logic gate (e.g., an inverter).

In Example 21, the OFETs of one or any combination of Examples 15-20 are disposed or connected so as to form an electronic circuit.

Thus, the present disclosure enables for the first time, the unexpected and surprising achievement of p-type doped donor-acceptor semiconducting copolymer(s) combined with n-type doped donor-acceptor semiconducting copolymer(s). The introduction of extrinsic charge-selective traps into a conjugated polymer capable of ambipolar transport enables attenuation of p- or n-type transport, while keeping the mobility of the desired charge carriers largely unperturbed.

BRIEF DESCRIPTION OF THE DRAWINGS

Referring now to the drawings in which like reference numbers represent corresponding parts throughout:

FIGS. 1(a)-1(d) illustrate PCDTPT:PC$_{61}$BM blends reduce electron current without drastically impacting hole current, wherein FIG. 1(a) shows transfer characteristics of a pristine PCDTPT OFET device (the PCDTPT device was bias-swept; the first scan is the red trace and the 20$^{th}$ scan is the blue trace); FIG. 1(b) shows the molecular structure of PCDTPT; FIG. 1(c) shows the transfer characteristics of a 95:5 wt. % PCDTPT:PC$_{61}$BM blend OFET device (the PCDTPT:PC$_{61}$BM device was bias-swept, the first scan is the red trace and the 20$^{th}$ scan is the blue trace); and FIG. 2(d) shows transfer characteristics of a PCDTPT OFET device and a 95:5 wt. % PCDTPT:PC$_{61}$BM device on a benzocyclobutene (BCB)-based polymer dielectric.

FIG. 4(c) shows the turn-on voltage shifts by ~15-20 V whereas the nearly unipolar blend measured in FIG. 4(d) shows shifts of ~5-8 V.

FIG. 9(f) illustrates lower power dissipation because current doesn't always flow in all parts of the circuit (in this case, no current flow in the n-OFET), FIG. 9(g) illustrates current flows when switching (in this case when P=Vin>threshold voltage Vt for the n-OFET device), FIG. 9(h) illustrates the maximum power point at the switching point P, FIG. 9(i) illustrates P=Vin approaching the threshold voltage Vt for the p-OFET, and FIG. 9(j) illustrates the p-OFET is off and no power dissipation. FIGS. 9(k)-9(l) illustrates that threshold voltage shifts during operation (e.g., a 5 V shift of Vt for the n-OFET) leads undesirable ambiguity in the binary state (e.g., less "0" state and more "1" state).

DETAILED DESCRIPTION OF THE INVENTION

In the following description of the preferred embodiment, reference is made to the accompanying drawings that form a part hereof, and in which is shown by way of illustration a specific embodiment in which the invention may be practiced. It is to be understood that other embodiments may be utilized and structural changes may be made without departing from the scope of the present invention.

Technical Description

One or more embodiments of the present invention relate to U.S. Utility patent application Ser. No. 15/400,579, filed Jan. 6, 2017, by Michael J. Ford and Guillermo Bazan, entitled "STABLE ORGANIC FIELD-EFFECT TRANSISTORS BY INCORPORATING AN ELECTRON-ACCEPTING MOLECULE", which application claims the benefit under 35 U.S.C. Section 119(e) of U.S. Provisional Patent Application No. 62/276,145, filed Jan. 7, 2016, by Michael J. Ford and Guillermo Bazan, entitled "STABLE ORGANIC FIELD-EFFECT TRANSISTORS BY INCORPORATING AN ELECTRON-ACCEPTING MOLECULE," (referred to hereafter as the 579' application. Specifically, the 579' application describes casting from blends of PCDTPT (molecular structure shown in FIG. 1(b)) and $PC_{61}BM$ and that $PC_{61}BM$ functioned as an effective electron trap, which reduced electron current and switched ambipolar transport of PCDTPT to p-only transport (FIGS. 1(a), 1(c) and 1(d)). The effect was demonstrated[8] on a $SiO_2$ dielectric and a polymer dielectric (FIG. 1). The 579' application also found the blends with an effective electron trap reduce bias-stress effects and are effective for a variety of fullerene acceptors, non-fullerene acceptors, and polymer semiconductors[34].

The present disclosure now shows that n-type only transport can also be achieved in a similar way. As described herein, introducing an effective hole trap reduces hole current without significant changes in electron current, switching ambipolar transport to n-type transport.

Figure 1A:
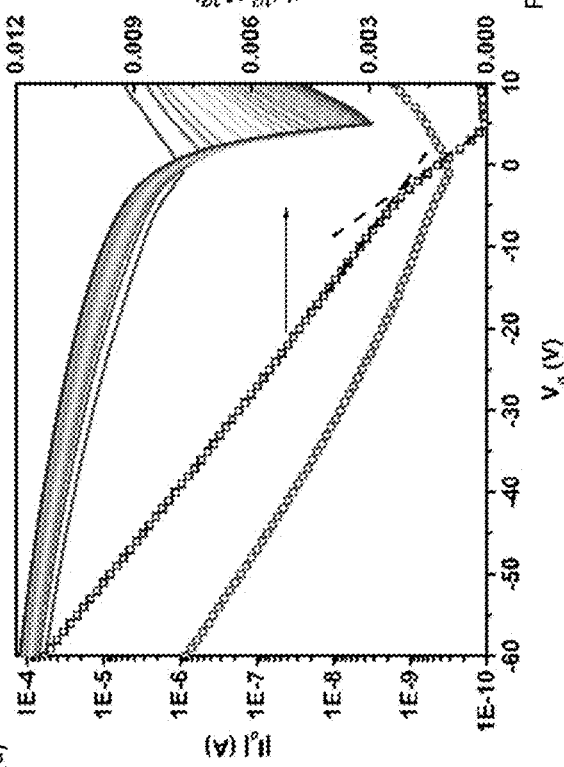
Figure 1B:
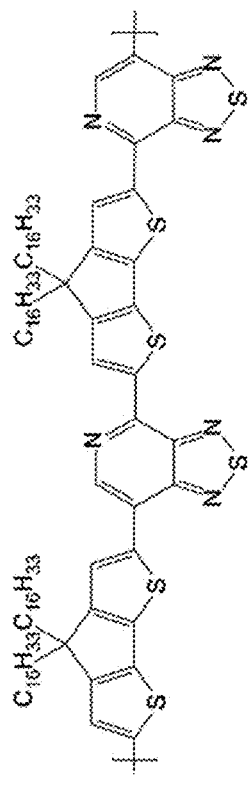
Figure 1C:
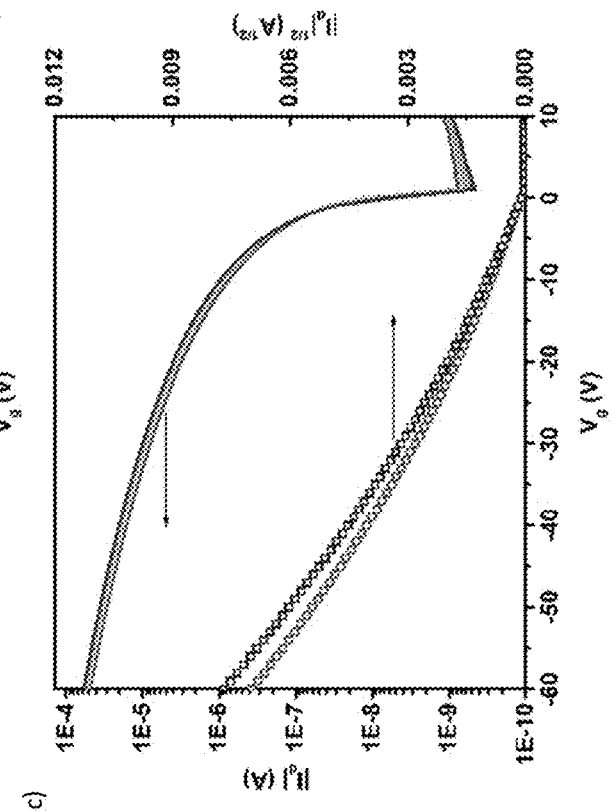
Figure 1D:
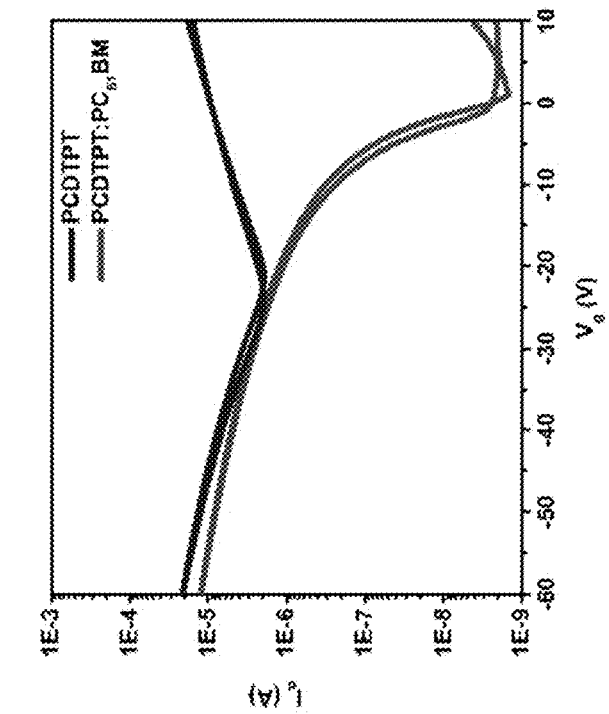
Figure 2A:
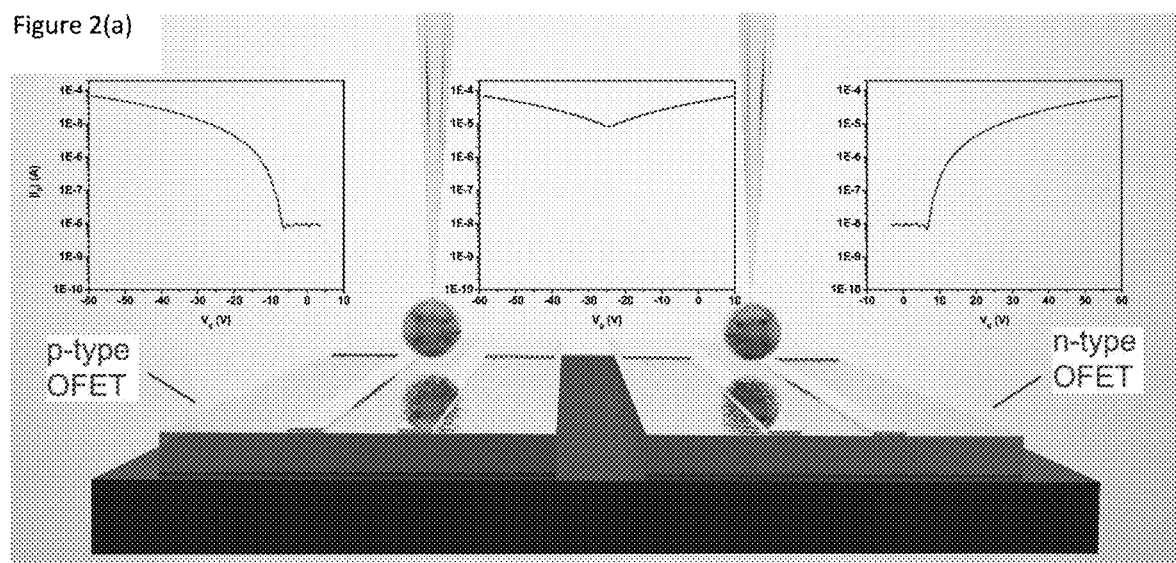
FIG. 2(a) is a schematic of solution-processed complementary OFETs with simulated saturation regime transfer curves for a p-type OFET (red), an ambipolar OFET (purple), and an n-type OFET (blue), wherein ambipolar conduction is characterized by relatively large |i$_d$| at both positive and negative V$_g$, while p-type transport operates only at negative V$_d$ and V$_g$ and n-type transport operates only at positive V$_d$ and V$_g$.
Figure 2B:
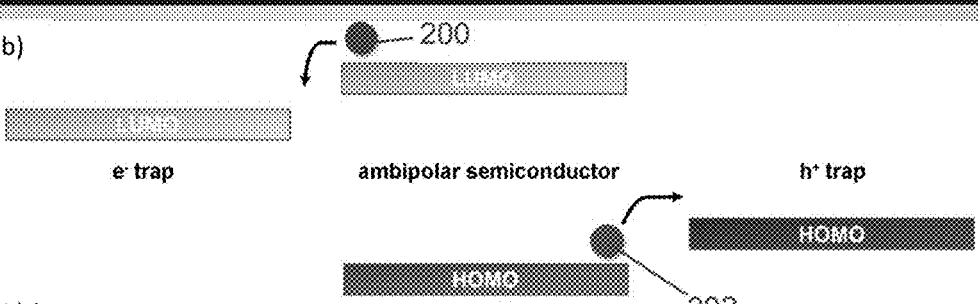
FIG. 2(b) is a schematic energy diagram that illustrates the molecular orbital requirements for electron (red, 200) and hole (blue, 202) traps used to enforce unipolar transport.
Figure 2C:
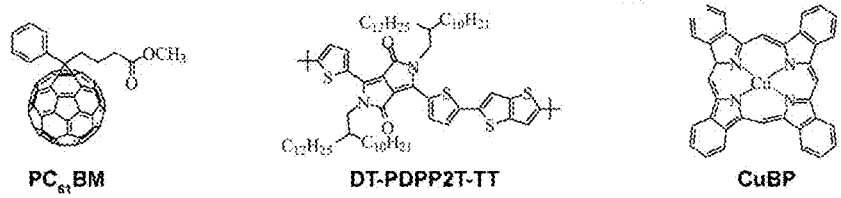
FIG. 2(c) illustrates molecular structures of the semiconducting polymer and additives used in one or more embodiments.

FIGS. 2(a)-2(c) shows the approach for managing the relative contribution of respective charge carriers. Ambipolar conduction in OFETs is characterized by a gate-modulated drain current ($I_d$) under both positive and negative gate voltages ($V_g$), as illustrated by the simulated $I_d$-$V_g$ plot shown in purple in FIG. 2(a). The strategy for achieving selective n-type transport involves a suitable hole trap that would be co-deposited with the polymer in order to impede p-type transport without impacting electron current. Under these conditions one would anticipate a reduction of current at negative $V_g$ (blue plot in FIG. 2(a)). This concept builds on the previous use of electron traps to achieve current-voltage stability through bias-stressing, but also has the added benefit of maintaining hole current and decreasing current at positive $V_g$ (red plot in FIG. 1a).[20] As illustrated in FIG. 2(b), a reasonable guide for choosing suitable electron traps is to implement molecules (or polymers) that have a lower lying lowest unoccupied molecular orbital (LUMO) relative to the host ambipolar semiconductor.[20] Conversely, a suitable hole trap would require the presence of a highest occupied molecular orbital (HOMO) that lies higher in energy with respect to the host material. This simple, solution-processing method of obtaining unipolar n-type transport is significant, given the difficulty of managing n-type transport relative to p-type transport as highlighted by recent review articles.[21] The concept of hole trapping in organic semiconductors has seldom been considered since adverse hole trapping has not been as problematic as electron trapping and carrier trapping is generally considered a problem to be avoided.[22] By selecting the appropriate additives, trapping can be advantageous and be used to control transport, as demonstrated herein. Appropriate HOMO and LUMO offsets are met with the set of materials shown in FIG. 2(c): DT-PDPP2T-TT (ambipolar polymer, HOMO=−5.1 eV, LUMO=−3.7 eV),[23] phenyl-C61-butyric acid methyl ester ($PC_{61}BM$, electron trap, LUMO=−3.7--4.3 eV)[20] and copper tetrabenzoporphyrin (CuBP, hole trap, HOMO=−4.4 eV).[24]

How inclusion of traps impacts charge carrier transport was examined by using bottom-gate/top-contact OFETs with a semiconductor layer that was spin-coated and then annealed at 200° C.

Results

1. Devices Comprising PCDTPT

Figure 3B:
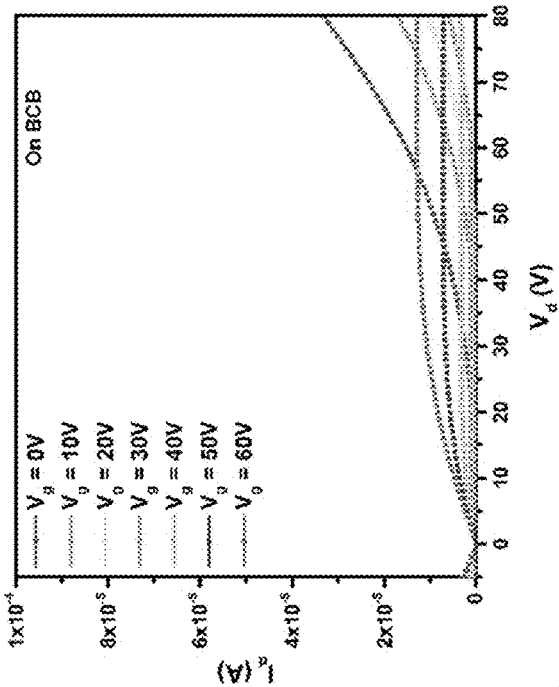
FIG. 3(b) shows n-type output characteristics of a PCDTPT bottom-gate top-contact (BCB, Ag, respectively) OFET, wherein the current has been normalized by the channel length and width in FIG. 3(a) to match the scale of FIG. 3(b)

OFETs in the bottom-gate, bottom-contact configuration with $SiO_2$ as the dielectric and gold as the source-drain contacts were fabricated to investigate electron conduction in PCDTPT. The n-type output characteristics of the first scan in FIG. 3(a) shows that n-type transport does not turn on until a gate voltage ($V_g$) of ~90 V is applied. Since PCDTPT on $SiO_2$ is susceptible to bias-stress effects (affecting electron conduction[35]) and gold may not be a suitable contact for electron injection into PCDTPT, n-type conduction was improved by switching to a bottom BCB gate dielectric and top contact silver source-drain contacts (see FIG. 3(b) for the n-type output characteristics). FIG. 3(c) shows the transfer characteristics of a p- and n-type conduction OFET comprising PCDTPT on $SiO_2$ and BCB and is used to compare the suitability of each dielectric and contact for n-type transport. With gold contacts and $SiO_2$, PCDTPT displays a reduced turn-on voltage for p-type transport at a drain voltage ($V_d$) of −80 V, and an increased turn-on voltage for n-type transport at $V_d$=+80 V (relative to PCDTPT on BCB with silver contacts). Therefore, PCDTPT can exhibit electron transport once the choice of dielectric and contacts are optimized.

In one or more device embodiments comprising PCDTPT, a suitable hole acceptor has a highest occupied molecular orbital (HOMO) energy level lying closer to vacuum than the HOMO energy level of PCDTPT. The HOMO energy level of PCDTPT has been measured to be ~5.1 Ev.[36] Various compounds were screened to investigate their efficacy as hole traps, including tetrathiafulvalene (TTF), which is widely-known to be an effective hole-transporting material,[37] and Spiro-OMeTAD (referred to here as Spiro), which is a known hole-transporting material with a HOMO energy value of 5.0 eV.[38] These materials were blended with PCDTPT in various wt. %, and cast onto a BCB dielectric with top contact silver electrodes.

Figure 3D:
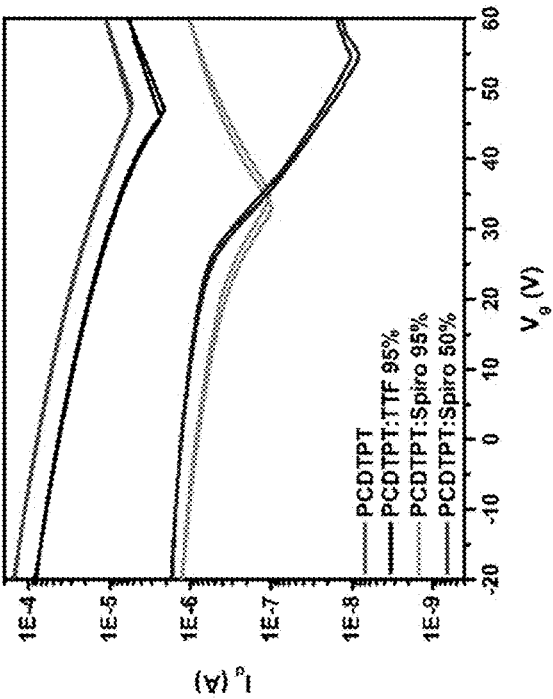
FIG. 3(d) shows n-type transfer characteristics of PCDTPT:hole trap blend devices with wt. % given relative to PCDTPT content.
Figure 3A:
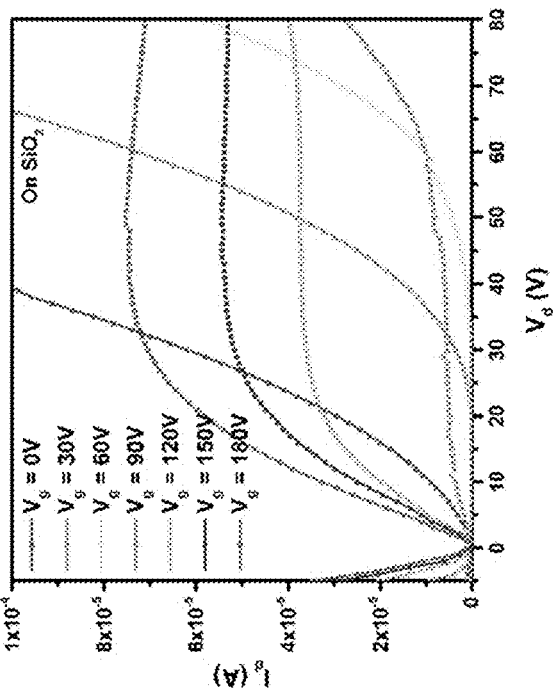
FIG. 3(a) shows n-type output characteristics of a PCDTPT bottom-gate bottom-contact (Sift, Au, respectively) OFET.
Figure 3C:
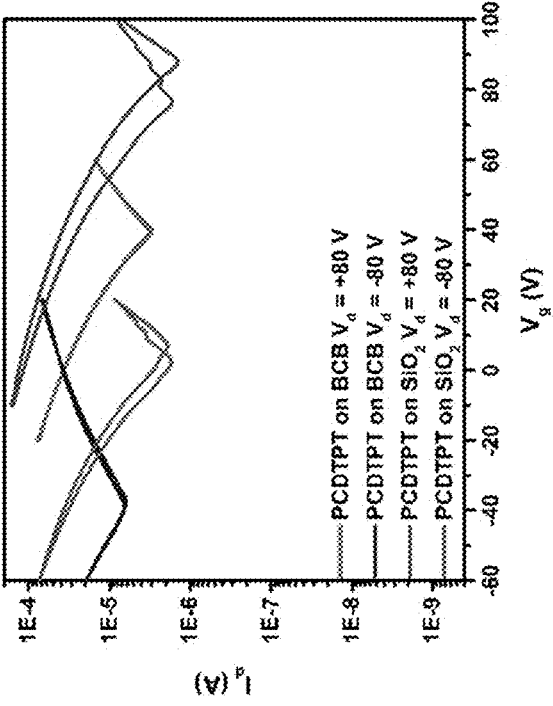
FIG. 3(c) shows transfer characteristics of n- and p-type OFETs on BCB and $SiO_2$.

FIG. 3(d) displays the device transfer characteristics. The hole conduction was monitored by observing the current between $V_g$=0 to −20 V. Addition of TTF reduces hole current by a factor of ~2; electron current is also reduced by the same magnitude. A 95:5 wt. % of PCDTPT:Spiro reduces hole current by a factor of ~100; electron current is reduced by a factor of ~10. A 50:50 wt. % of PCDTPT:Spiro does not change hole current relative to 95:5 wt. % PCDTPT:Spiro, but electron current is further reduced. Therefore, Spiro in optimized wt. % concentrations (likely dependent on other factors such as the blend morphology, semiconductor mobility, and HOMO offset) is a suitable hole trap in polymer semiconductor blends.

2. Devices comprising DT-PDPP2T-TT

In one or more embodiments, a combination of hole traps and PCDTPT may be inadequate for producing n-only devices, even when using the improved conditions of BCB dielectric and Ag contacts. Therefore, OFETs were fabricated from blends of hole trapping molecules with DT-PDPP2T-TT, which was reported to have an electron mobility of 1.5 cm$^2$ V$^{-1}$s$^{-1}$.[39]

Figure 4A:
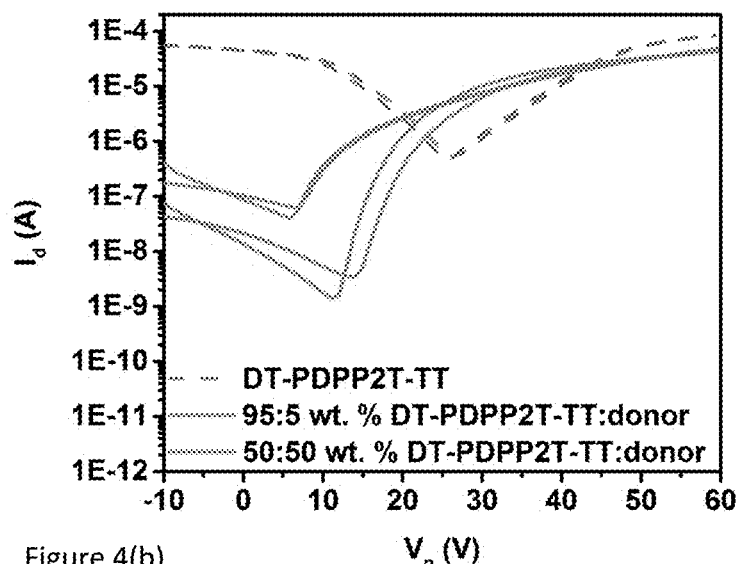
FIG. 4(a) shows transfer characteristics of bottom-gate/top-contact DT-PDPP2T-TT:CuBP OFETs at $V_d$=80 V, illustrating a reduction of hole conduction by CuBP without similar decreases in electron conduction to produce unipolar n-type OFETs from an ambipolar polymer (pristine DT-PDPP2T-TT is shown for reference).
Figure 4B:
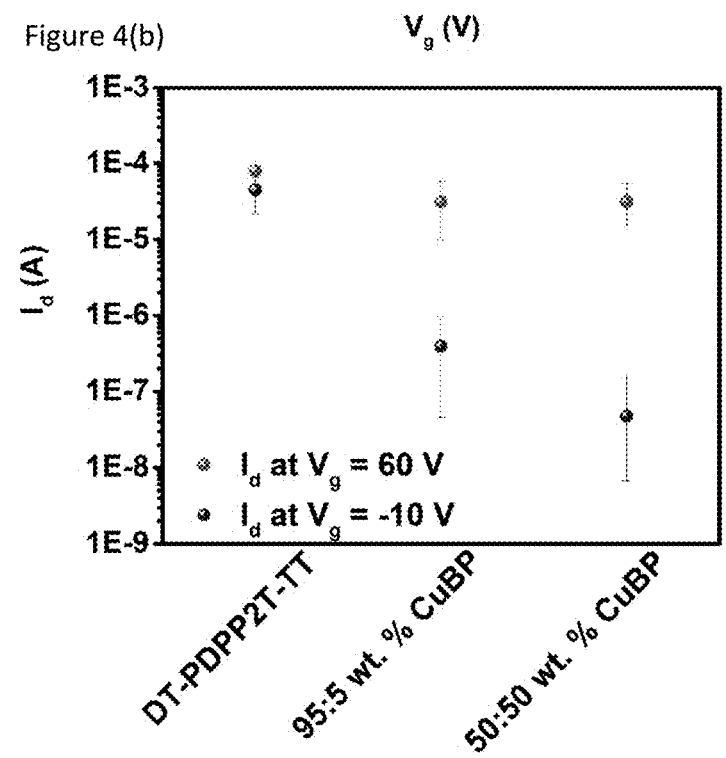
FIG. 4(b) shows the average peak hole ($V_g$=−10 V) and electron currents ($V_g$=60 V) for different blend conditions, wherein peak electron current remains fairly constant progressing from $8\times10^{-5}$ A to $3\times10^{-5}$ A to $3\times10^{-5}$ A, while peak hole current is reduced from $4\times10^{-5}$ A to $5\times10^{-7}$ A to $4\times10^{-8}$ A as the additive content increases, errors bars represent the minimum and maximum values measured, and all OFETs were measured with identical device architecture and geometry: channel length and width of 2.5 mm and 160 μm)

Measurements of $I_d$ as a function of $V_g$ (primarily $V_g$>0) with $V_d$=80 V (FIG. 4(a), grey trace) and the gradual channel approximation equation[25] were used to estimate the electron mobility of DT-PDPP2T-TT ($\mu_e$, 0.33±0.11 cm$^2$ V$^{-1}$s$^{-1}$). A typical transfer curve for pristine DT-PDPP2T-TT, shown in FIG. 4(a), exhibits an $I_d$-$V_g$ dependence indicative of balanced ambipolar transport; hole conduction, which is maximized at $V_g$<0, matches electron conduction ($V_g$>0). Simultaneous charge injection of both carriers results in $I_{ON}/I_{OFF}$ in the range of 10$^1$-10$^2$ (Table 1). FIG. 4(b) further emphasizes the balanced ambipolar transport by showing the similarity in peak electron current ($I_d$ at $V_g$=60 V, ~8×10$^{-5}$ A) and hole current ($I_d$ at $V_g$=−10 V, ~4×10$^{-5}$ A).

a. DT-PDPP2T-TT:CuBP

Copper tetrabenzoporphyrin (CuBP) was blended with DT-PDPP2T-TT as a hole trapping compound. CuBP is cast from a soluble precursor CuCP that converts to CuBP after annealing.[40]

Figure 4C:
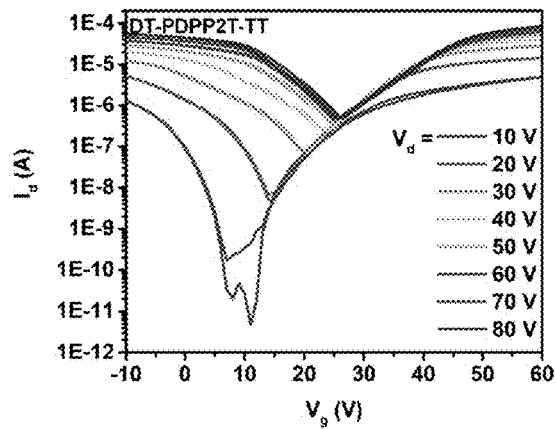
FIGS. 4(c)-4(d) show transfer characteristics of DT-PDPP2T-TT and a 50:50 wt. % DT-PDPP2T-TT:CuBP blend, wherein curves were measured with different values of $V_d$ to investigate the turn-on voltage dependence of the two systems.
Figure 4D:
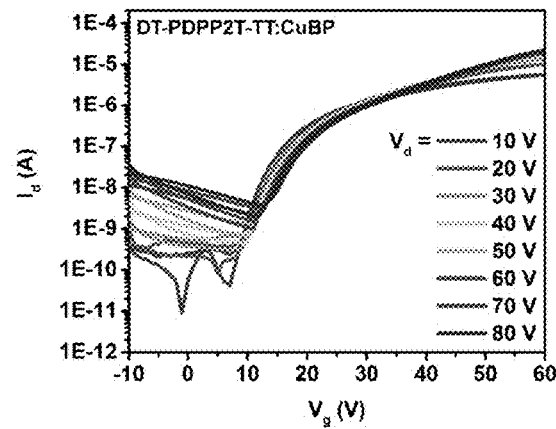
Figure 4E:
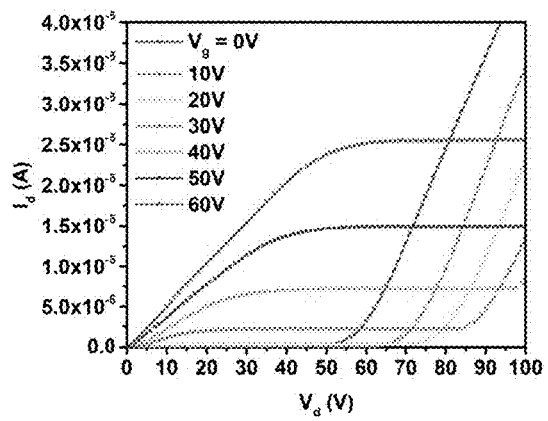
FIGS. 4(e)-4(f) show output characteristics of DT-PDPP2T-TT (FIG. 4(e)) and 95:5 wt. % DT-PDPP2T-TT:CuBP blend (FIG. 4(f)). Note the improved saturation for the blend OFET.
Figure 4F:
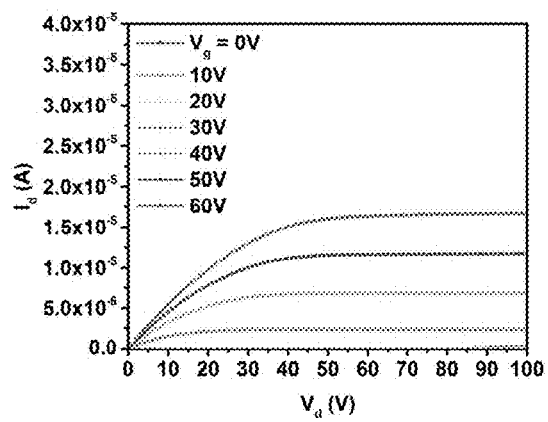
Figure 4I:
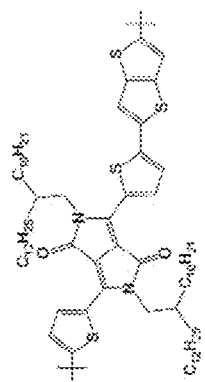
FIG. 4(i) shows the molecular structure of DT-PDPP2T-TT.

CuBP was introduced with blend ratios of 95:5 wt. % and 50:50 wt. % DT-PDPP2T-TT:CuBP. The resulting blends were annealed for 10-30 seconds at 200° C. to optimize charge transport in the polymer and the trapping efficiency of CuBP. FIG. 4(a) compares the OFETs characteristics for these blends, relative to those of pristine DT-PDPP2T-TT. Examination of $I_d$ vs. $V_g$ shows that the incorporation of 5 wt. % CuBP leads to an increase of $I_{ON}/I_{OFF}$ to up to 10$^3$. Increasing CuBP to 50 wt. % increases $I_{ON}/I_{OFF}$ to up to 10$^4$ without substantial changes in $\mu_e$ (Table 1). Differences in $I_d$ vs. $V_g$ characteristics can also be appreciated by examination of FIG. 4(b), which reveals a decrease of the peak hole current from ~4×10$^{-5}$ A to 5×10$^{-7}$ A (95:5 wt. %) or 4×10$^{-8}$ A (50:50 wt. %), while maintaining an average peak electron current of 3×10$^{-5}$ A. Note that comparisons of absolute current values are relevant while keeping the dielectric material, dielectric thickness, and device dimensions constant, which is the case here. In addition, while ambipolar transport results in a turn-on voltage that depends on $V_d$ (FIGS. 4(c) and 4(d)), the blend strategy mitigates such a $V_d$-dependence on turn-on voltage. Output characteristics (FIGS. 4(e)-4(f)) demonstrate improved current saturation for the blend OFET relative to the pristine OFET. These data are consistent with a reduction of hole conduction and a minimal perturbation in electron transport in DT-PDPP2T-TT upon addition of CuBP.

Figure 4H:
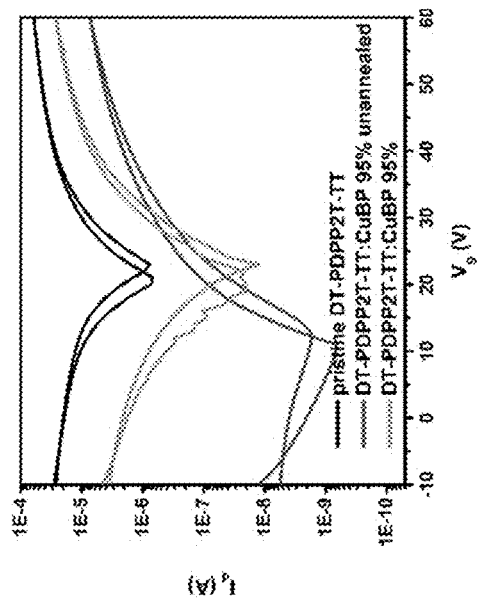
FIGS. 4(g)-4(h) show transfer characteristics for an OFET comprising DT-PDPP2T-TT blended with Spiro with various wt. % concentrations (FIG. 4(g)) and an OFET device comprising DT-PDPP2T-TT blended with CuBP at 95:5 wt. % DT-PDPP2T-TT:CuBP (FIG. 4(h)), wherein annealed and unannealed blends are also shown.

FIG. 4(h) shows 95:5 wt. % DT-PDPP2T-TT:CuBP has hole conduction reduced by ~10 as compared to pristine DT-PDPP2T-TT. Unannealed devices were also investigated, and exhibit hole current reduced by an order of 5000 as compared to the devices using pristine DT-PDPP2T-TT. Electron current, and thus electron mobility, is also reduced by an order of magnitude.

TABLE 1

OFET characteristics for different blend compositions. Average values are calculated from at least 11 devices for each condition and the resulting standard deviations are provided.

|  | DT-PDPP2T-TT | 95:5 wt. % CuBP | 50:50 wt. % CuBP |
|---|---|---|---|
| $\mu_e$ (cm$^2$ V$^{-1}$ s$^{-1}$) | 0.33 ± 0.11 | 0.30 ± 0.21 | 0.16 ± 0.07 |
| $I_{ON}/I_{OFF}$ | 10$^1$-10$^2$ | 10$^2$-10$^3$ | 10$^2$-10$^4$ | b. DT-PDPP2T-TT: Spiro

Figure 4G:
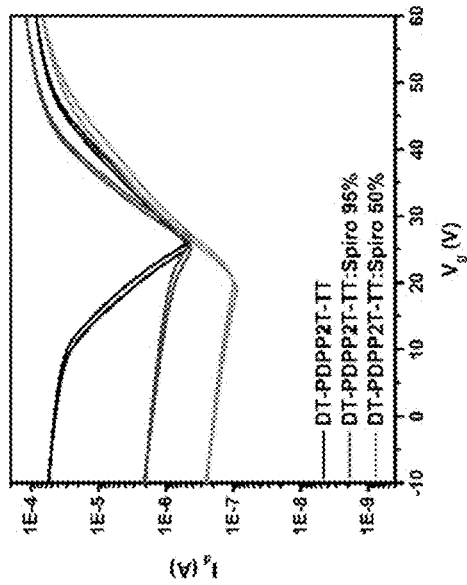

FIG. 4(g) shows that 95:5 wt. % DT-PDPP2T-TT:Spiro has hole conduction reduced by a factor of ~30 relative to pristine DT-PDPP2T-TT. The electron conduction is unchanged with an average mobility of 1.9±0.4 cm$^2$ V$^{-1}$s$^{-1}$. Pristine DT-PDPP2T-TT was measured to have an average mobility of 2.1±0.4 cm$^2$ V$^{-1}$s$^{-1}$. The hole conduction of 50:50 wt. % DT-PDPP2T-TT:Spiro is further reduced (by a factor of ~200 as compared to pristine DT-PDPP2T-TT). However, the average electron mobility of 50:50 wt. % DT-PDPP2T-TT:Spiro is also slightly reduced to a mobility of 1.0±0.2 cm$^2$ V$^{-1}$s$^{-1}$.

Figures 5A, 5B, 5C:
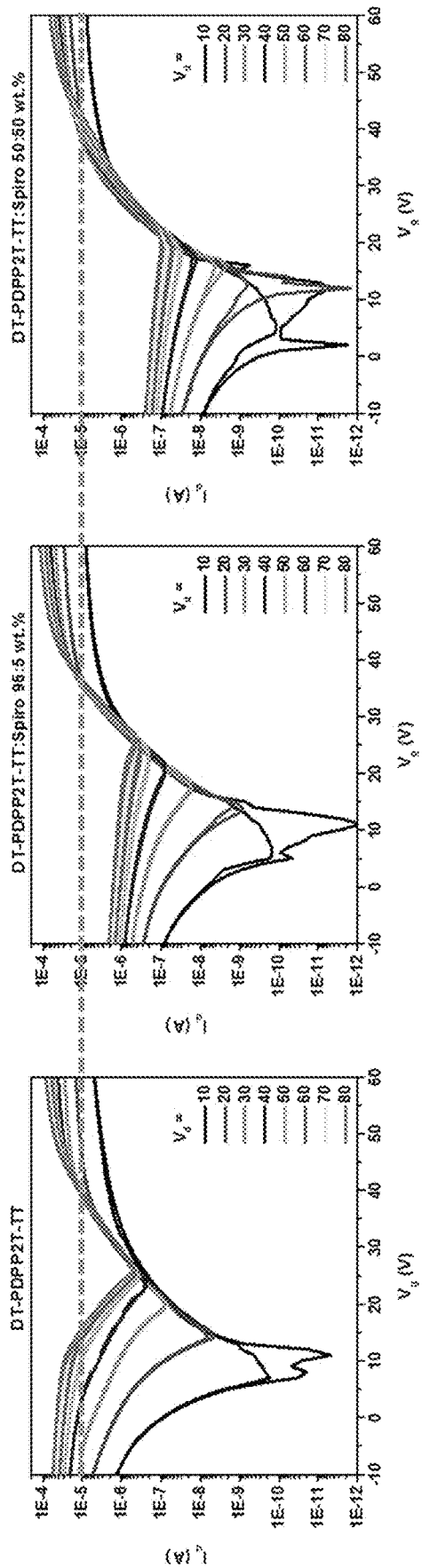
FIGS. 5(a)-5(c) show n-type transfer characteristics of OFET devices, for an OFET comprising DT-PDPP2T-TT (FIG. 5(a)), for an OFET comprising DT-PDPP2T-TT blended with Spiro (95:5) wt. % (FIG. 5(b); and an OFET comprising DT-PDPP2T-TT blended with Spiro (50:50) wt. % (FIG. 5(c); for various $V_d$ and wherein a dotted line has been drawn as a visual aid to compare the hole conduction at $V_d$=30 V.

FIGS. 5(a)-5(c) show transfer characteristics at various $V_d$ for OFETs comprising pristine DT-PDPP2T-TT, 95:5 wt. % DT-PDPP2T-TT:Spiro, and 50:50 wt. % DT-PDPP2T-TT: Spiro, respectively, and further emphasize reduction in hole current.

A maximum ON/OFF ratio of 3000 was obtained for the 50:50 wt. % blend; for pristine DT-PDPP2T-TT the maximum ON/OFF ratio was 240.

The data presented herein shows that Spiro is as an effective hole trap but requires selection of a desired wt. % if a balance between on/off ratio and mobility is desired.

c. Dependence on annealing time

Figure 6:
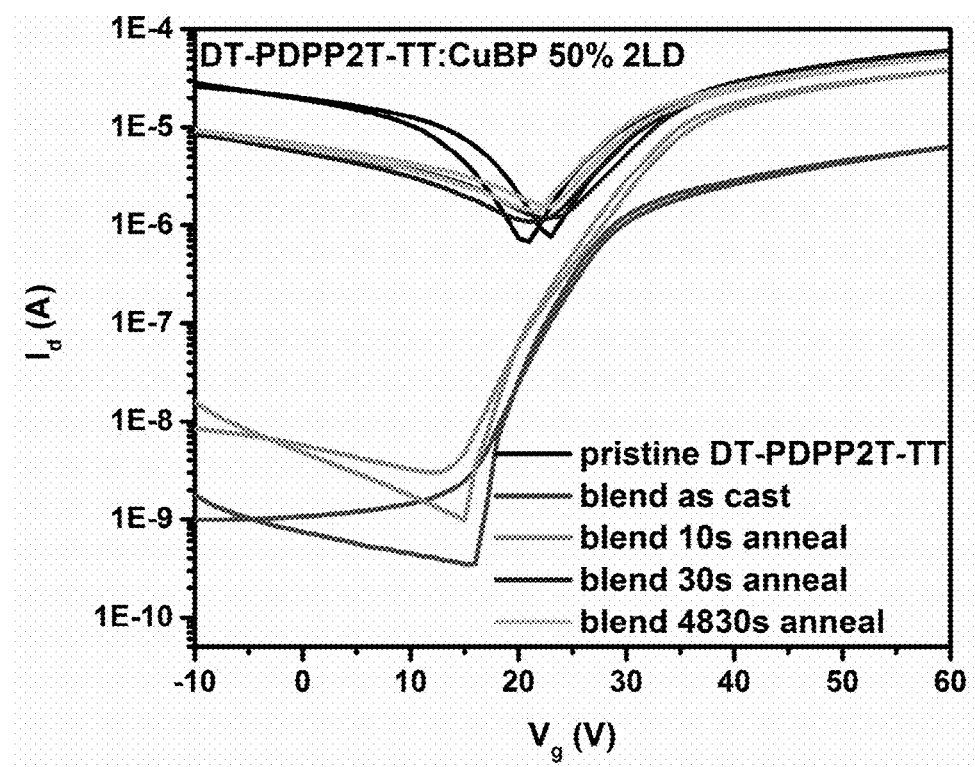
FIG. 6 shows output characteristics for OFET devices comprising DT-PDPP2T-TT:CuBP (precursor) blends annealed at 200° C. for periods of 10 seconds(s), 30 s, and 4830 s (CuCP, the CuBP precursor was used for device fabrication because it's higher solubility that CuBP. CuCP was converted to CuBP during thermal annealing at 200° C., partially (10 s annealing) or completely (4830 s annealing).).
Figure 7A:
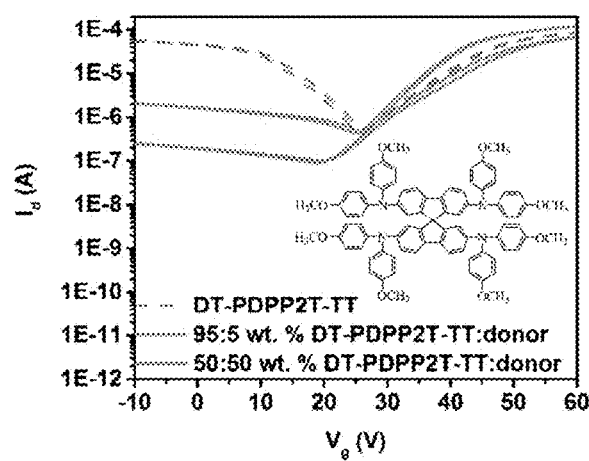
FIGS. 7(a)-7(d) show transfer characteristics of OFETs comprising DT-PDPP2T-TT:Spiro-MeOTAD blends annealed for 8 min (FIG. 7(a)), PCDTPT(structure shown): CuBP blend cast by sequential deposition on top of PCDTPT with PCDTPT annealed for 10 s for reference (FIG. 7(b)), DT-PDPP2T-TT:CuBP blend with a lower molecular weight DT-PDPP2T-TT batch used (FIG. 7(c)), and lower molecular weight DT-PDPP2T-TT:tetrabenzoporphyrin blend (FIG. 7(d)). These results demonstrate that different polymer: additives combinations can be used. All OFETs were fabricated with identical device architectures and dimensions as those described in the main text.
Figure 7B:
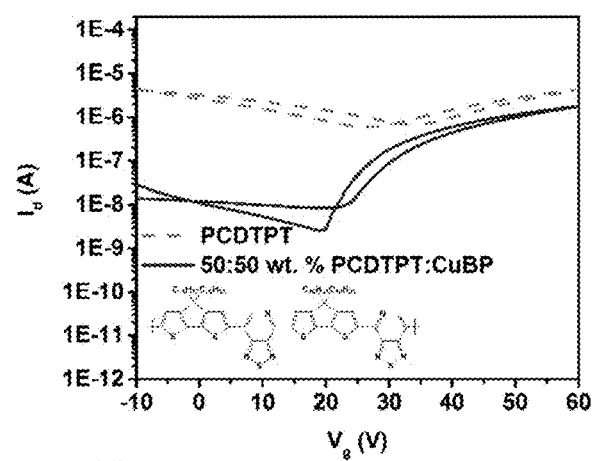
Figure 7C:
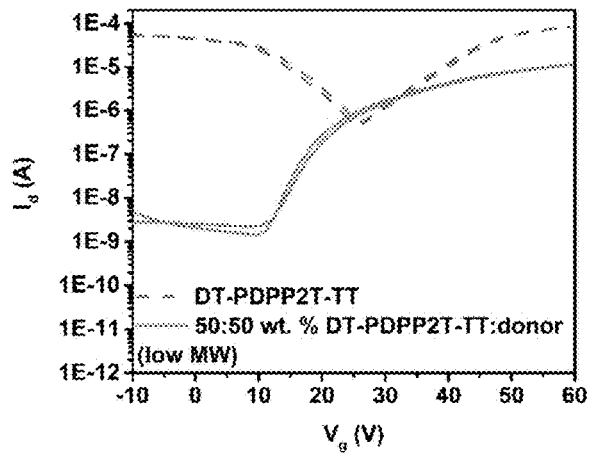
Figure 7D:
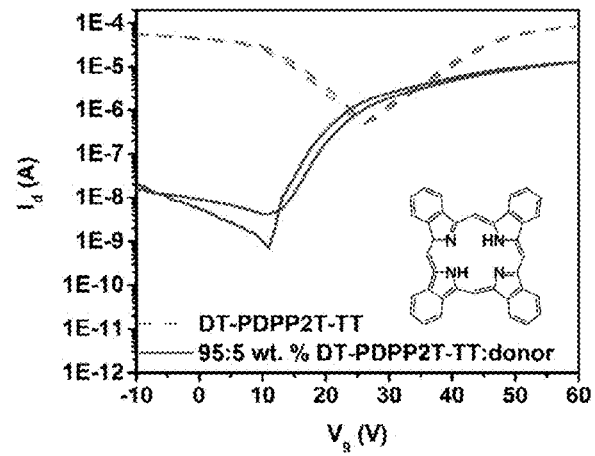

To optimize the electron current without impacting the reduction in hole conduction, one or more embodiments of the present invention attempted various annealing times (as shown in FIG. 6). A two-layer deposition (2LD) device was cast, where the DT-PDPP2T-TT:CuCP blend was spun "on-the-fly" (i.e., while the substrate is already spinning) on top of an already-cast pristine DT-PDPP2T-TT OFET. Hole conduction in this case was reduced by 10000 as compared to pristine DT-PDPP2T-TT. Annealing for 10 seconds improved the electron current by an order of magnitude. Further annealing improved electron current to match pristine DT-PDPP2T-TT but also increased hole conduction. It may be that the precursor acts as a better hole trap, which could be due to a lower mobility or more optimized morphology for trapping. Again, the data presented herein shows that a careful balance between on/off ratio and mobility can be maintained with control of the hole trapping compound.

d. Additional Data

Further studies were performed to further explore the generality of the additive-based technique. FIGS. 7(a)-7(d) compare the performance of devices comprising Spiro-MeOTAD (HOMO=−4.9 eV)[26] blended with DT-PDPP2T-TT to obtain a 95:5 and 50:50 wt. % blend, PCDTPT (HOMO=−5.1 eV)[20] blended with CuBP, DT-PDPP2T-TT:CuBP blended with a lower molecular weight DT-PDPP2T-TT, and a lower molecular weight DT-PDPP2T-TT:tetrabenzoporphyrin blend.

As discussed above, the data shows the DT-PDPP2T-TT:SpiroMeOTAD OFETs with blend compositions of 95:5 and 50:50 exhibited increased $I_{ON}/I_{OFF}$ values relative to the pristine DT-PDPP2T-TT (from $10^1$-$10^2$ to $10^3$ while $\mu_e$ remains constant). The electron current is similar to electron current in the pristine DT-PDPP2T-TT ($1 \times 10^{-4}$ and $6 \times 10^{-5}$ A for the 95:5 and 50:50 wt. % blends, respectively, using identical device architecture and geometries as used to obtain the data in FIG. 4(a)). However, the average hole current is reduced by up to 2 orders of magnitude, to $3 \times 10^{-6}$ and $3 \times 10^{-7}$ A, for the 95:5 and 50:50 wt. % blends, respectively.

The general trends observed upon introduction of a hole trap were also observed when PCDTPT was used in combination with CuBP. As discussed above, PCDTPT has a lower $\mu_e$ (0.03 cm$^2$ V$^{-1}$s$^{-1}$) than DT-PDPP2T-TT, but it also exhibits ambipolar behavior with an $I_{ON}/I_{OFF}$ of $10^1$. Upon addition of 5 wt. % CuBP, $I_{ON}/I_{OFF}$ increases to $10^2$-$10^3$ while $\mu_e$ is relatively unchanged. For further comparison, the peak hole current is reduced from $6 \times 10^{-6}$ A to $3 \times 10^{-8}$ A without substantial changes in average peak electron current, which was $4 \times 10^{-5}$ A in both cases. These results highlight that the introduction of hole traps provides a general method to discontinue p-transport, while maintaining viable electron transport pathways.

Example Electronic Circuit

The present disclosure further describes a complementary inverter taking advantage of a single semiconducting polymer structure (e.g., DT-PDPP2T-TT blended with PC$_{61}$BM as an effective electron trap to produce an unipolar p-OFET[20], and DT-PDPP2T-TT blended with CuBP to fabricate a unipolar n-OFET). An inverter is a fundamental building block of logic circuits and switches a high voltage state ("1") to a low voltage state ("0") or vice-versa. Compared to complementary-like inverters that use ambipolar semiconductors, a complementary inverter that utilizes unipolar components, as described herein, benefits from wider noise margins that define the operational voltage range.

Figure 8A:
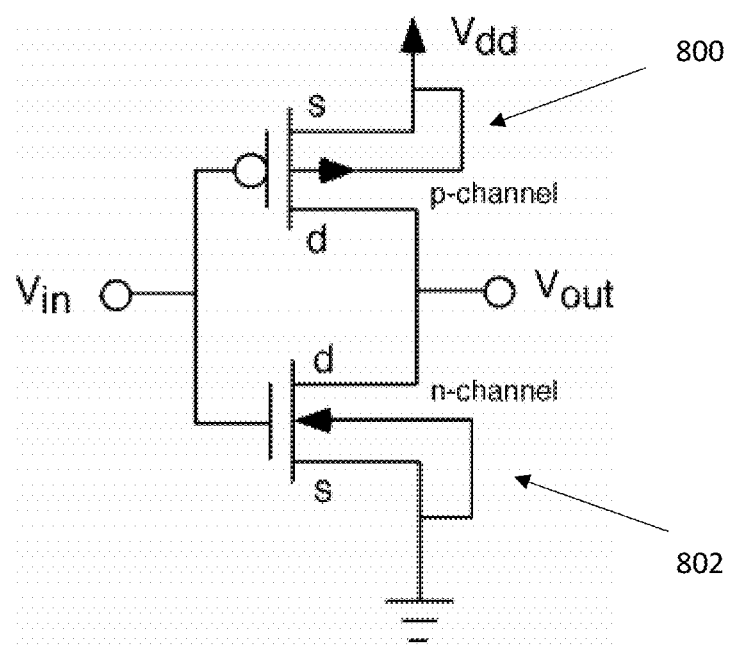
FIG. 8(a) illustrates an inverter circuit using OFETs according to one or more embodiments of the invention and FIG. 8(b) illustrates the inverter measurement. OFET gates are connected by Ag paste for inverters cast on two separate substrates.

FIG. 8(a) illustrates an inverter comprising an n-channel OFET 802 including a semiconducting polymer combined with a hole accepting compound (as described herein) connected to a p-channel OFET 800 including the electron accepting compound as described in the 579' application cross-referenced above.

In one fabricated example, the p-OFET/p-channel OFET 800 comprised 95:5 wt. % blend of DT-PDPP2T-TT:PC$_{61}$BM and the n-OFET/n-channel OFET 802 comprised a 95:5 wt. % blend of DT-PDPP2T-TT:CuBP). Each OFET was fabricated in a bottom-gate/top-contact configuration, using the polymer dielectric divinyl-tetramethyl-siloxane-bis(benzocylcobutene) (BCB) on SiO$_2$ and Ag top contacts. The semiconductor blend layers were spin-coated "on-the-fly" (i.e., the semiconductor blend solution was deposited while the substrate was already spinning) on top of the dielectric, from a 5 mg/mL solution at 2000 revolutions per minute (RPM). The semiconductor blend layers were then annealed at 200° C. The fabricated device architecture comprises doped Si/SiO$_2$(300 nm)/BCB(50 nm)/DT-PDPP2T-TT/Ag (80 nm).

The structures of DT-PDPP2T-TT, PC$_{61}$BM, CuCP and CuBP were as follows, while each R in CuCP is independently hydrogen or a substituted or non-substituted alkyl, aryl or alkoxy chain:

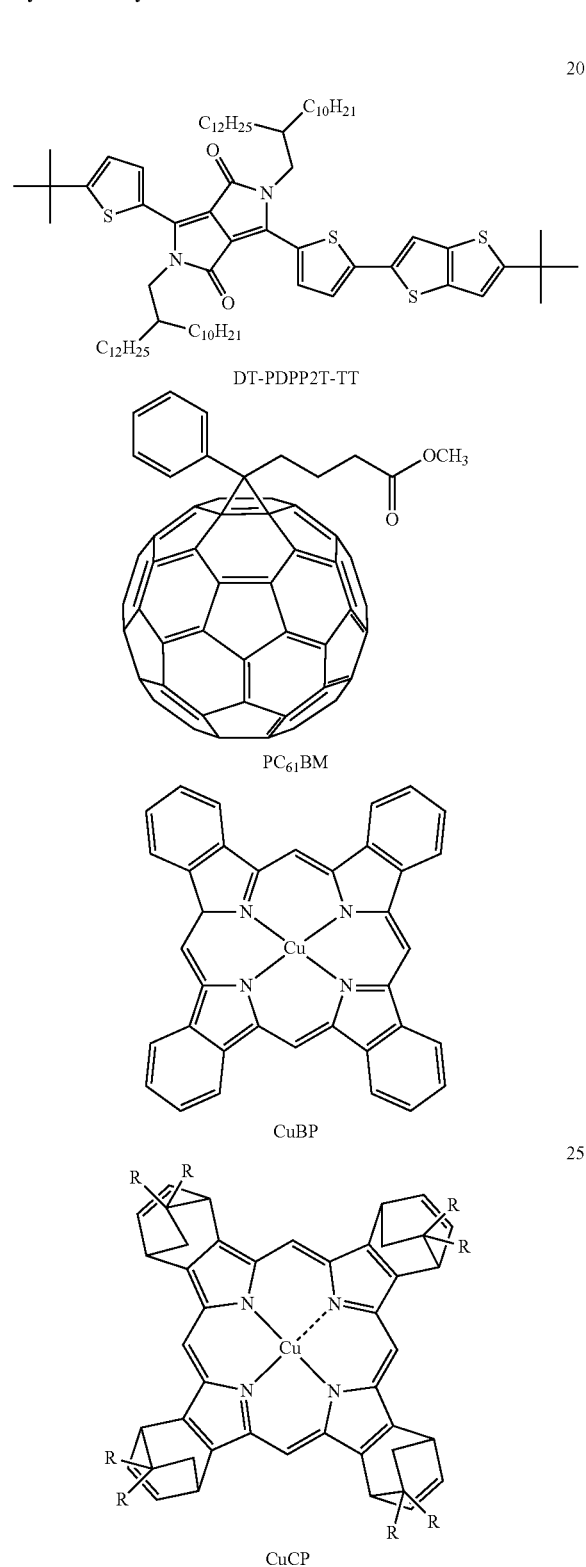

Figure 9A:
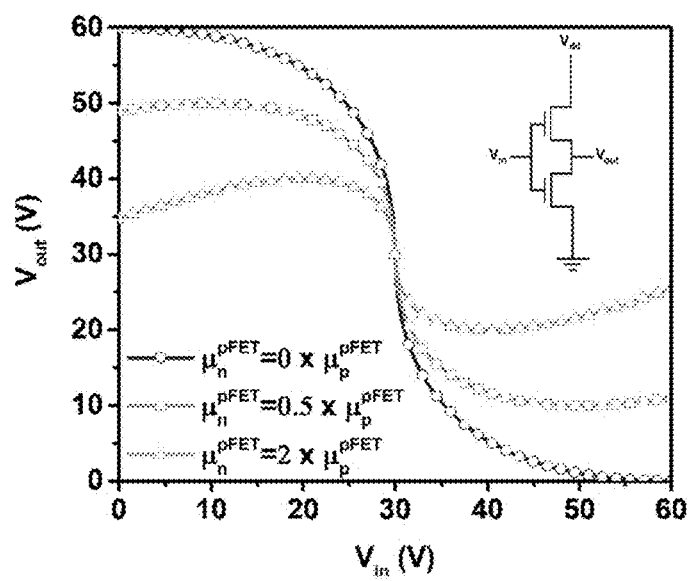
FIG. 9(a) shows simulated complementary inverter voltage transfer curves using a simple voltage divider model, wherein electron and hole mobility of the n-OFET and the p-OFET, respectively, are set equal. Ambipolar transport (orange and green traces) is considered by setting the electron mobility of the p-OFET ($\mu_n^{pFET}$) equal to different multiplicative factors of the hole mobility of the p-OFET ($\mu_p^{pFET}$). Inset shows the inverter circuit.

The OFETs were first tested individually before the complementary inverters were fabricated by connecting the p-OFETs 800 and n-OFETs 802 in series with a common gate (as shown in FIG. 8(a) and inset of FIG. 9(a)). The significance of this embodiment is highlighted by the fact that both blend OFETs were fabricated using identical processing procedures, including annealing conditions, gate dielectric, source/drain contacts and device dimensions.

The gate voltage, now functioning as the input voltage ($V_{in}$) was swept while a constant supply voltage ($V_{dd}$) was applied and the output voltage ($V_{out}$) was measured. The performance of inverters is often quantified in terms of the gain (the first derivative of $V_{out}$ with respect to $V_{in}$), which has an impact on the noise margin of the device and hence the yield of logic circuits when multiple elements are combined.[27]

Inverter characteristics were compared to inverters made from pristine polymer OFETs. A gain of 180 was achieved for the blend OFET components, similar to the pristine polymer OFET. However, the OFETs comprising the blends exhibited advantageously higher high on/off ratio and balanced threshold voltages. The OFETs comprising the blends also have larger noise margins so that the OFETs function across a wide range of input voltages Vin and output voltages Vout.

FIG. 9(a) is a plot of simulated voltage transfer curves (i.e., $V_{out}$ vs. $V_{in}$) where voltage losses and power dissipation, characterized qualitatively by non-saturation of the final "1" and "0" states, are observed when using ambipolar semiconductors.[27] Details of the model, which considers the OFETs as resistors and thus neglects factors such as saturation/linear regimes and threshold voltages, are given in the methods section below. For a p-OFET (or an n-OFET) with no ambipolar transport (blue trace), there are essentially no voltage losses since the "1" and "0" states reach saturation; the voltage transfer curves thus resemble a step function. Voltage losses increase if electron (hole) transport is viable in the original p-OFET (n-OFET), as characterized by deviations from the step function shape and an increase of the slope in the final states (orange, green traces; see methods section below for details on the calculation).[27] Therefore, in addition to high μ and invariant turn-on voltages, ambipolar transport should be discouraged for the individual p-OFET and n-OFET components since the resulting noise margin will be lower. These criteria are successfully met by using the blend strategy described herein.

Figure 9B:
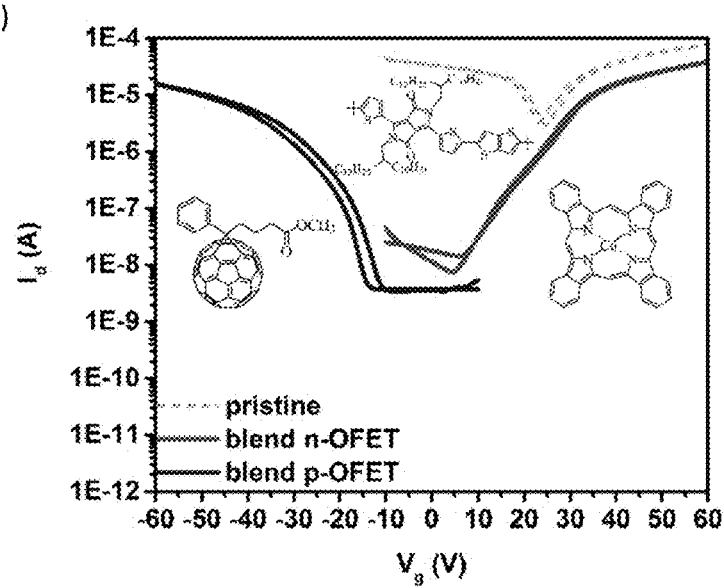
FIG. 9(b) shows transfer curves for an n-OFET (95:5 wt. % DT-PDPP2T-TT:CuBP blend) (red trace) and a p-OFET (95:5 wt. % DT-PDPP2T-TT:$PC_{61}BM$)(blue trace), wherein the pristine polymer OFET is shown for comparison and $|V_d|$=80 V.
Figure 9C:
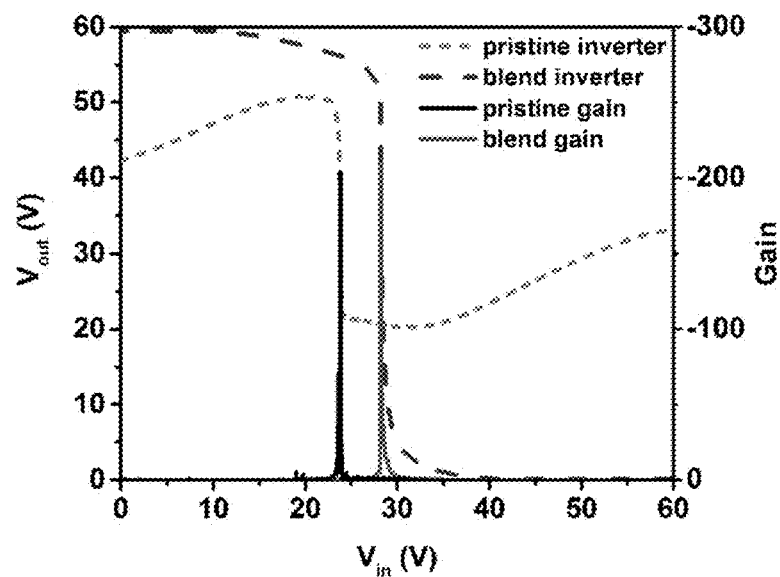
FIG. 9(c) shows transfer curves (dashed traces) and gain vs. Vin (solid traces) for inverters comprising pristine OFETs and 95:5 wt. % polymer:additive blend OFETs operated at $V_{dd}$=60 V, wherein $V_{out}$ (Volts, V) and $V_{in}$ (Volts, V) are measured at the locations indicated in FIG. 8(a), the active layer/channel in the pristine inverter comprises DT-PDPP2T-TT, the active layer/channel in the p-OFET in the blend inverter comprises DT-PDPP2T-TT combined with $PC_{61}BM$, and active layer/channel in the n-OFET in the blend inverter comprises DT-PDPP2T-TT combined with CuCP/CuBP.

FIG. 9(b) shows representative OFET characteristics of the two blend transistors, which display balanced transport properties and high $I_{ON}/I_{OFF}$ relative to the pristine OFET. An inverter that used pristine DT-PDPP2T-TT in both the n-OFET and p-OFET was fabricated and operated at $V_{dd}$=60V for reference, and the voltage transfer curve of this device (FIG. 9(c), grey dashed line) exhibits voltage losses as anticipated from the data presented in of FIG. 9(a). The inverter comprising a p-OFET with 95:5 wt. % DT-PDPP2T-TT:PC$_{61}$BM and an n-OFET with 95:5 wt. % DT-PDPP2T-TT:CuBP, on the other hand, exhibited a voltage transfer curve with near-ideal characteristics (FIG. 9(c), purple dashed line) and matched more closely to the blue trace in FIG. 9(a). Moreover, the gain for the blend inverter exceeds 200, a notable value for solution-processed complementary organic inverters (the pristine inverter has similar switching capabilities).

Figure 9D:
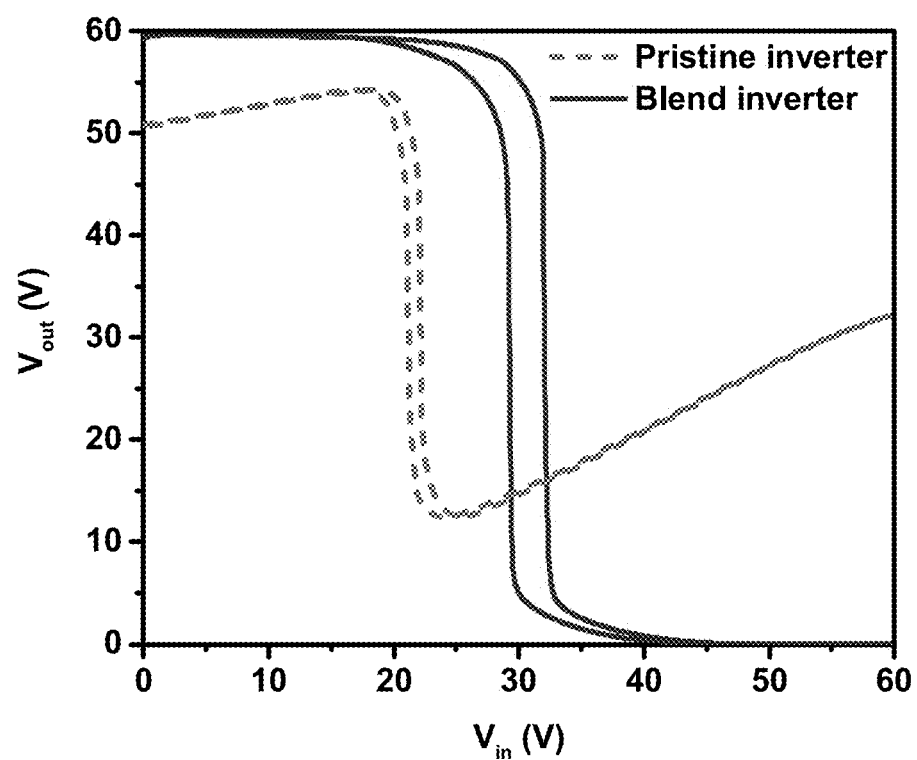
FIG. 9(d) compares the performance of an inverter comprising an OFET wherein the active layer/channel includes pristine ambipolar semiconducting polymers (prisitine inverter comprising DT-PDPP2T-TT) and an inverter comprising the OFETs wherein the active layer/channel includes a blend (blend inverter comprising DT-PDPP2T-TT and CuCP/CuBP or DT-PDPP2T-TT and $PC_{61}BM$ with 50:50 wt. % additive).
Figure 9E:
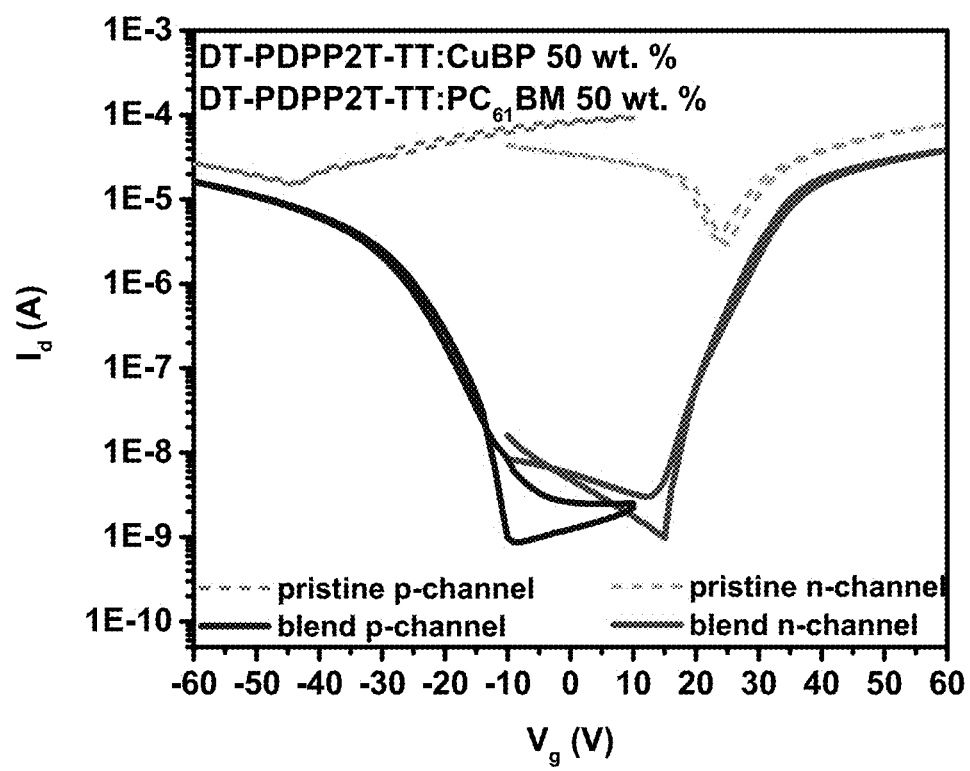
FIG. 9(e) shows data comparing the drain current ($I_d$) vs. gate voltage ($V_g$) characteristics of (1) an OFET wherein the active layer/channel comprises a pristine semiconducting polymer (DT-PDPP2T-TT), (2) an OFET wherein the active layer/channel comprises a semiconducting polymer blend for n-only transport (DT-PDPP2T-TT and CuCP/CuBP, 50 wt. %), and (3) an OFET wherein the active layer/channel comprises a semiconducting polymer for p-only transport (DT-PDPP2T-TT and $PC_{61}BM$ 50 wt. %), and wherein the OFETs are fabricated on BCB polymer dielectric and Ag top contacts are used.
Figure 9F:
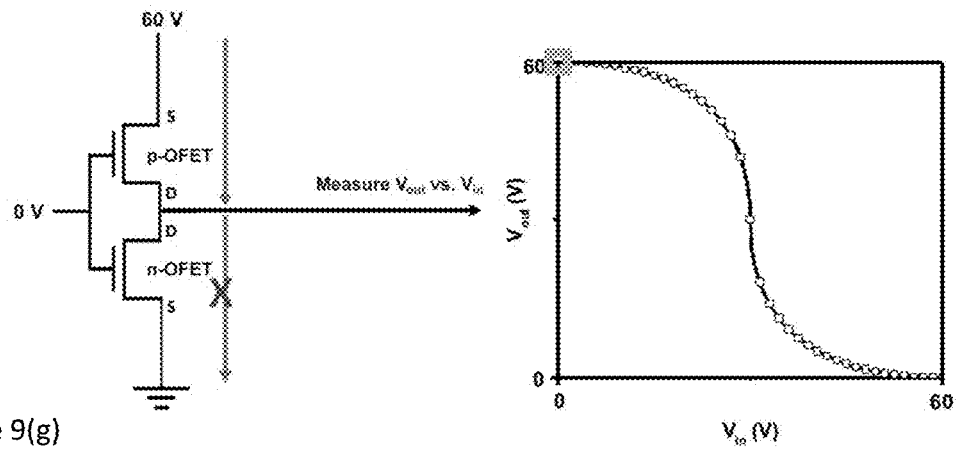
FIGS. 9(f)-9(l) illustrate the advantages of the inverter circuit comprising example blend OFETs described herein, wherein P illustrates the Vin in the various examples.
Figure 9G:
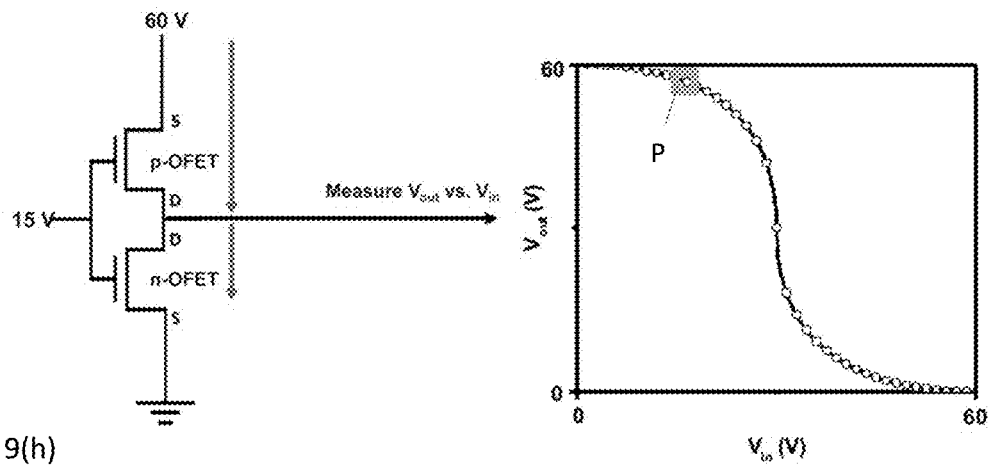
Figure 9H:
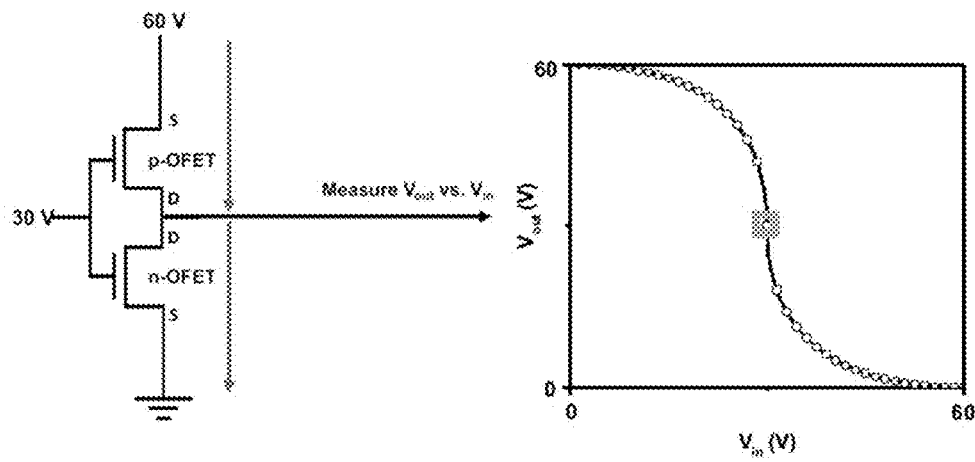
Figure 9I:
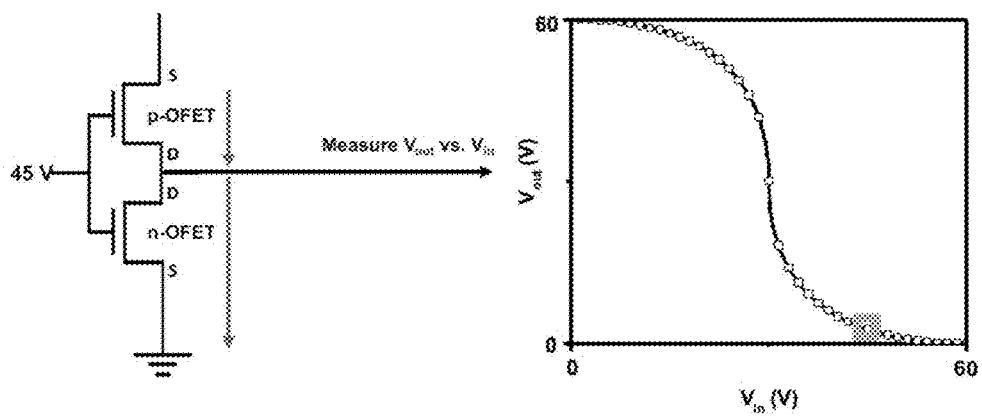
Figure 9J:
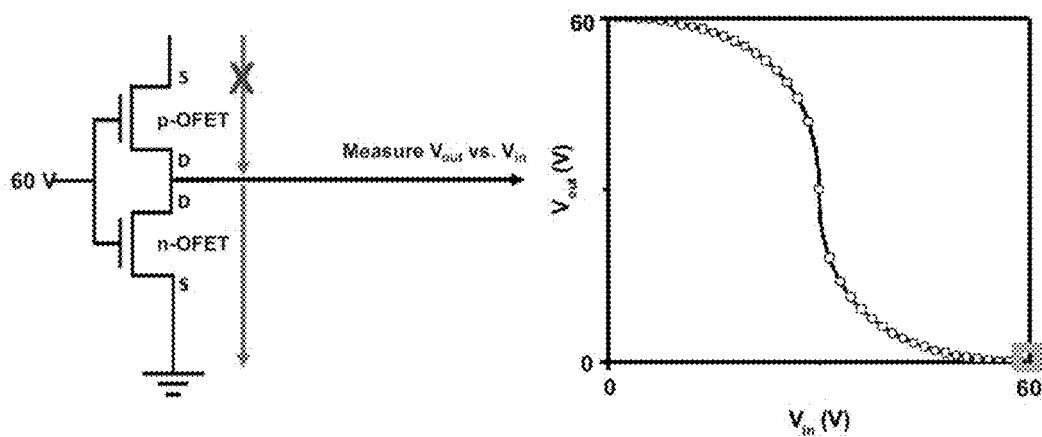
Figure 9K:
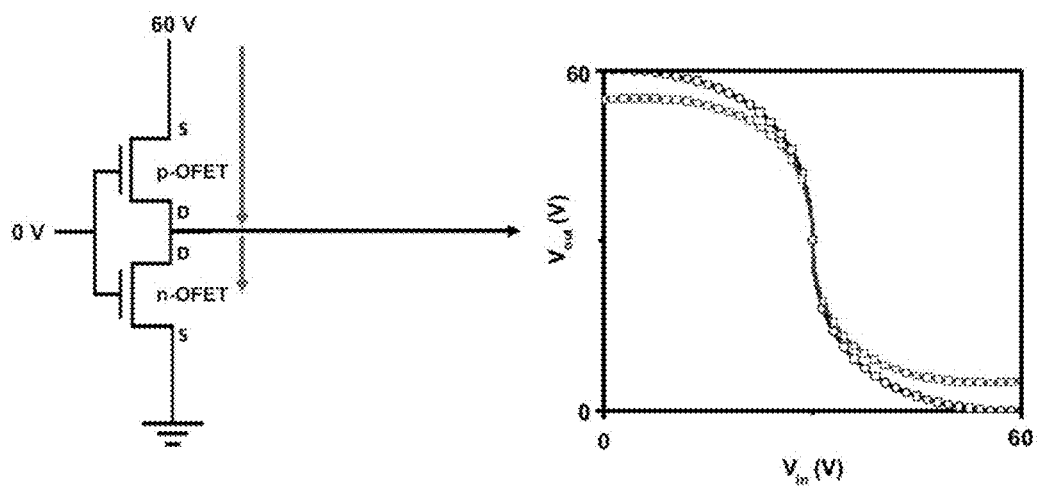
Figure 9L:
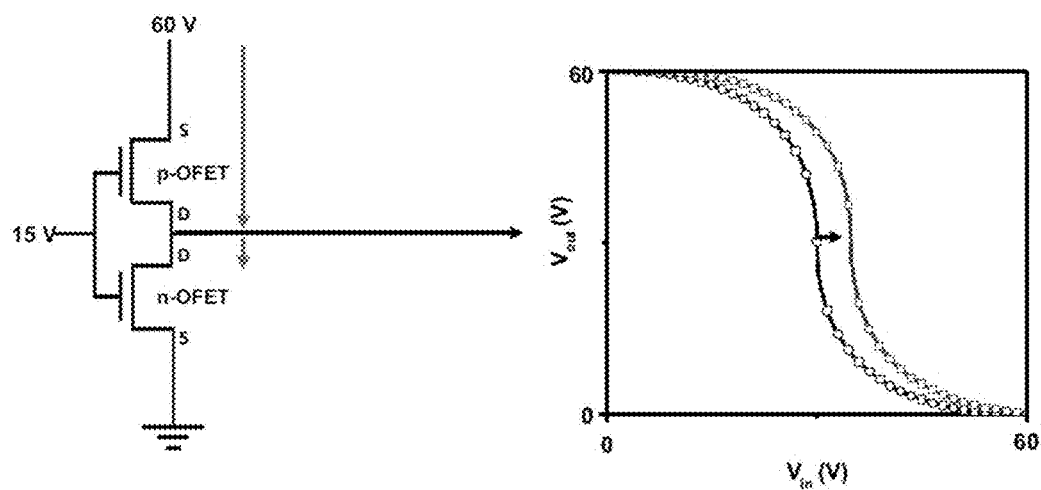

FIGS. 9(f)-9(l) illustrate the advantages of the inverter circuit comprising example blend OFETs described herein, wherein P illustrates the Vin in the various examples. FIG. 9(f) illustrates lower power dissipation because current doesn't always flow in all parts of the circuit (in this case, no current flow in the n-OFET), FIG. 9(g) illustrates current flows when switching (in this case when P=Vin>threshold voltage $V_t$ for the n-OFET device), FIG. 9(h) illustrates the maximum power point at the switching point P, FIG. 9(i) illustrates P=Vin approaching the threshold voltage Vt for the p-OFET, and FIG. 9(j) illustrates the p-OFET is off and no power dissipation. FIGS. 9(k)-9(l) illustrate that threshold voltage shifts during operation (e.g., a 5 V shift of $V_t$ for the n-OFET) leads undesirable ambiguity in the binary state (e.g., less "0" state and more "1" state). The blend devices described herein may have reduced or no threshold voltage shifts, overcoming this problem.

Figure 9M:
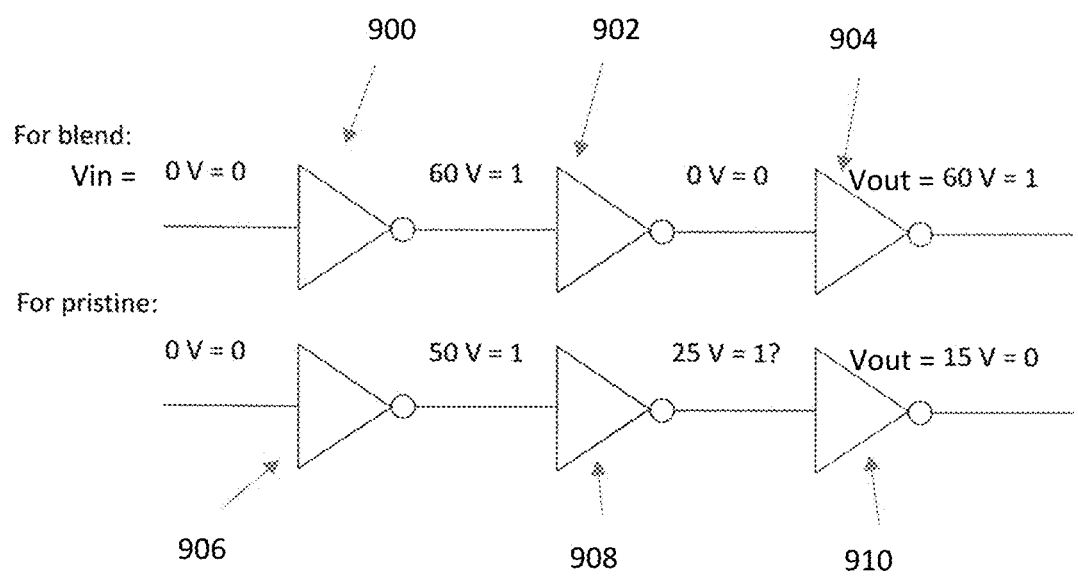
FIG. 9(m) shows the increased stability of OFETs using the blend compositions (the bias voltages required to switch the OFETs into each of the binary states is consistently the same for each OFET).

FIG. 9(m) illustrates a first chain of inverters 900, 902, 904 each comprising the circuit of FIG. 8(a) (using OFETs fabricated from blend compositions) and a second chain of inverters 906, 908, 910 each comprising OFETs fabricated from pristine ambipolar DT-PDPP2T-TT. The inverters are connected so that the output of an inverter is used as the input to the next inverter in the chain.

The input Vin to the first inverter 900, 906 is 0 V, corresponding to the binary "0" or OFF state. FIG. 9(m) shows that each inverter 900, 904 fabricated from the blend compositions repeatably converts an OFF signal input (Vin=0 V corresponding to binary state "0") into an ON output (Vout=60 V corresponding to binary state "1") and that inverter 902 converts Vin=60 V corresponding to binary "1" into a Vout=0 V corresponding to binary state "0". In one or more examples, the inverters fabricated from the blend compositions are stable because a single input voltage (e.g., 0 V) repeatably biases the inverter into an ON state (binary state"1") and a single input voltage (e.g., 60 V) repeatably biases the inverter into an OFF state (binary state "0") after multiple cycles of the gate between the binary states.

The inverters fabricated from the pristine ambipolar DT-PDPP2T-TT, on the other hand, would not have reliable operation. Specifically, inverter 908 would not be able to invert the on signal (binary "1") into an off signal (binary "0"). Thus, the inverters comprising pristine semiconducting polymer are unstable because different gate voltages (0 V, 50 V) bias the inverter in an ON state and different input voltages (25 V) bias the inverter in an OFF state (see FIG. 9(d)).

Figure 10A:
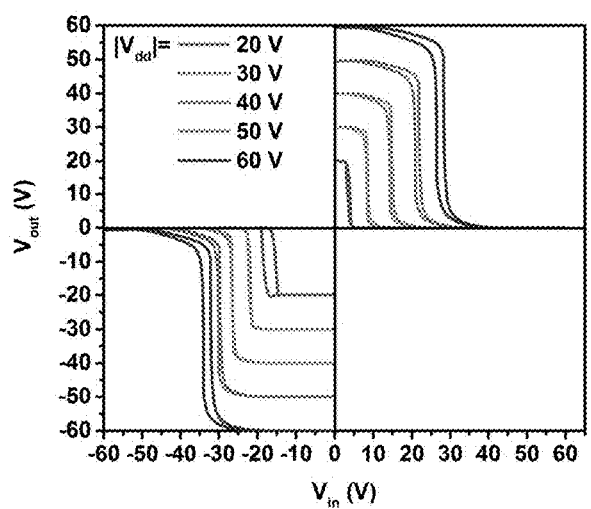
FIGS. 10(a)-10(b) show inverter characteristics measured at different values of $V_{dd}$. All OFETs were fabricated with identical device architectures and dimensions as in the main text.
Figure 10B:
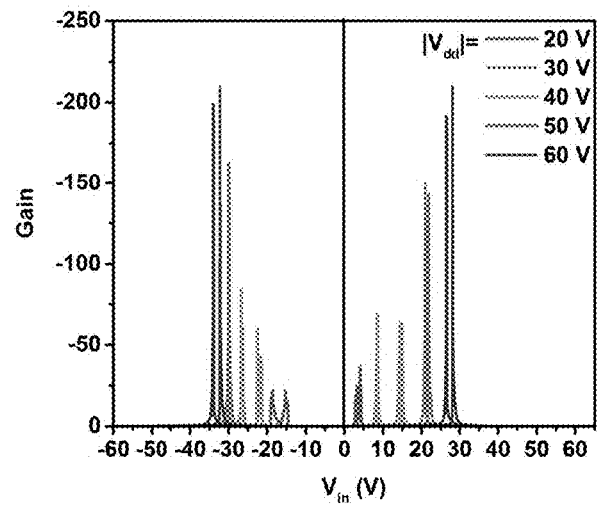

The switching voltage of the blend devices is also almost exactly half of the supply voltage (28 V) when VDD is 60 V. This indicates well-balanced hole and electron motilities in the respective transistors and is desirable for a high-noise margin. FIGS. 10(a)-10(b) show the low hysteresis inverter characteristics observed for the blend devices. FIGS. 10(a)-10(b) also show inverters from the blend solutions can operate at low $V_{dd}$ with gain >10 when $V_{dd}$≥20 V, making such configurations suitable for applications requiring lower voltages.[27,28] Since no voltage loss is observed in the blend inverter, the noise margin, which defines the operational voltage range for the "1" and "0" states, can be estimated for the blend inverter using the largest square method.[25] The inverter measured in FIG. 9(c) has a noise margin of 20 V (67% of maximum), surprisingly and unexpectedly similar to the noise margin of some of the best performing complementary organic semiconductor based inverters (characterized by ~75% noise immunity[28,29]). The broad noise margins, along with the excellent switching characteristics and high gain observed in the blend based inverters disclosed herein, are promising properties for all-organic complementary circuits.

Figure 10C:
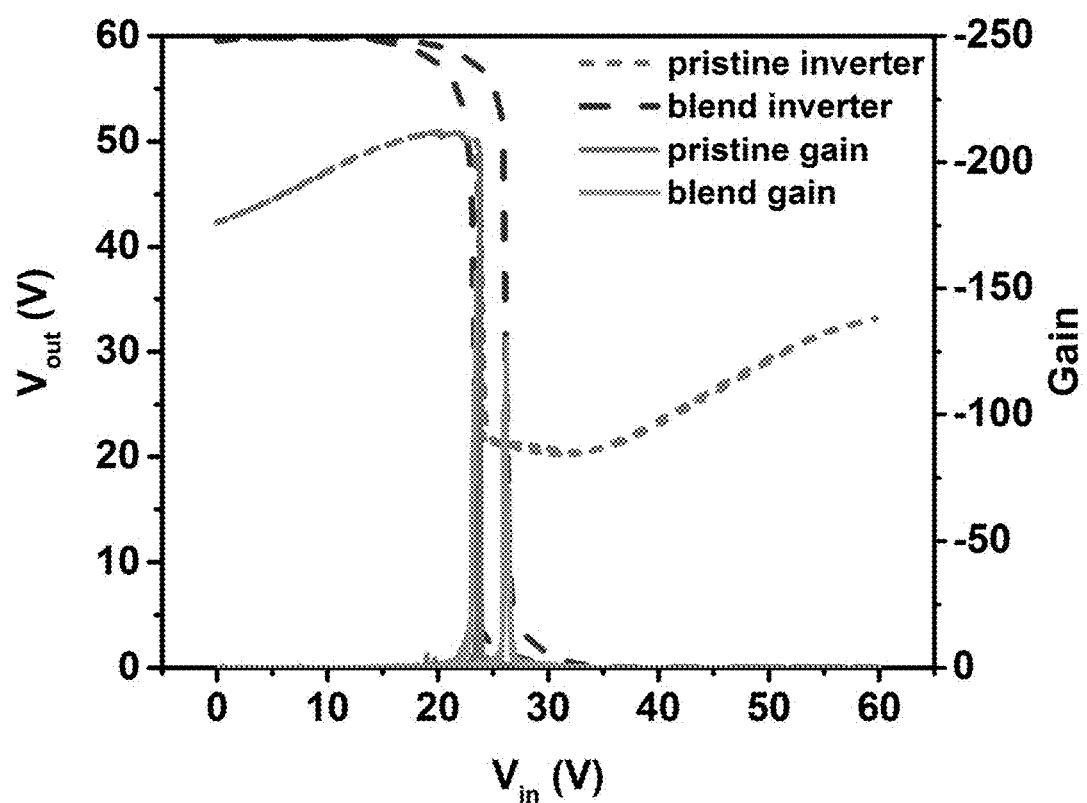
FIG. 10(c) shows inverter characteristics for inverter fabricated from two blend OFETs cast onto a single substrate by blade-coating. The forward and backward trace of the blend inverter is shown.
Figure 11:
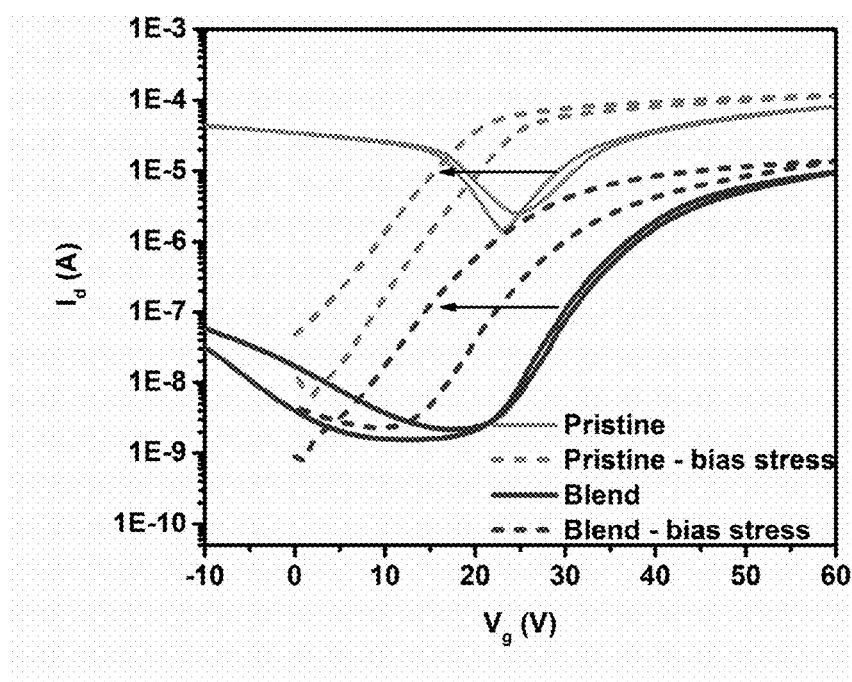
FIG. 11 shows results of a bias stress experiment on 95:5 wt. % DT-PDPP2T-TT:CuBP blend and pristine DT-PDPP2T-TT OFETs. Devices were scanned after annealing and then subsequently bias stressed at $V_g$=−60 V for ca. 10 s. Vt was taken from the forward scan before and after biasing. For the pristine OFET, $\Delta V_t$=11.9 V; for the blend OFET, $\Delta V_t$=15.1 V.

The solution-processable inverters fabricated above did not require additional dielectric treatment or evaporation steps, and could be fabricated atop polymer dielectric layers with identical device architectures and processing conditions. Thus, this methodology for complementary organic electronics fabrication may be advantageous relative to other techniques that require selective dielectric surface modification or different source-drain contacts for the respective p- and n-OFETs.[18,19,27,28] While FIGS. 10(a)-10(b) show data for inverters comprising p- and n-components fabricated via spin-coating onto separate substrates, the present disclosure has also fabricate inverters via blade-coating deposition of the n- and p-components onto a single substrate (as illustrated in the graphic in FIG. 2(a)). Such a method is anticipated to be more amenable to high-throughput fabrication relative to spin-coating. FIG. 10(c) shows the resulting inverter characteristics are similar in terms of performance (gain 136-157).

Figure 12B:
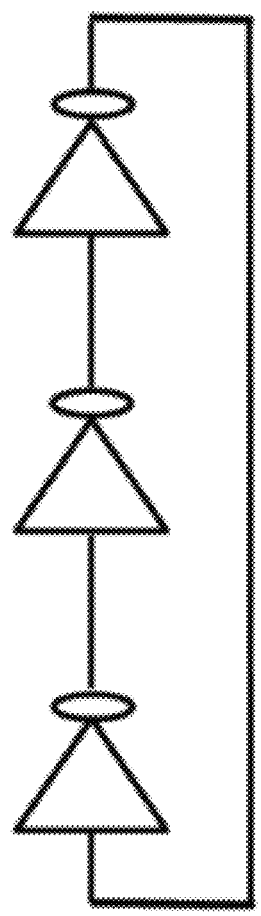
FIG. 12(a) illustrates an SRAM memory device and FIG. 12(b) illustrates a ring oscillator.
Figure 12A:
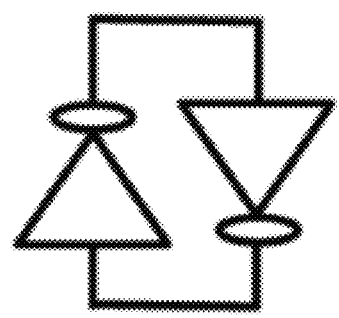

Other devices (such as a memory device or ring oscillator) could be fabricated using (1) the combination of blends described herein with the blends described in the 579' application (e.g., p-n junctions) or (2) using only the n-type blends described herein (e.g., n-type OFETs). FIG. 12(a) illustrates a memory device (SRAM) for storing the state of the inverter without much power and FIG. 12(b) illustrates a ring oscillator (e.g., for synchronizing computation and timing applications).

Example Methods

The following methods and materials were used to obtain the data in described herein (unless indicated otherwise). Materials were purchased or synthesized according to previous procedures.[36]

a. Device Fabrication

Semiconductor Materials: With the exception of PCDTPT, which was synthesized from previous procedures[30], all materials were obtained through commercial means. Spiro-MeOTAD was purchased through Sigma-Aldrich. The soluble precursors for CuBP and tetrabenzoporphyrin were provided by Mitsubishi Chemicals. DT-PDPP2T-TT was purchased from 1-Materials.

A 300 nm $SiO_2$ dielectric/doped Si (University Wafer) substrate was sonicated in acetone and isopropanol for 3 minutes in each solvent. The substrates were dried by $N_2$ and placed in a 120° C. oven for 10 min, after which they underwent UV-$O_3$ cleaning for 15 minutes. The BCB dielectric material (also referred to as Cyclotene 3022-46) was purchased from Dow Chemicals and diluted by volume to a ratio of 1:46 with toluene. The dielectric layer was spun at 4000 RPM and dried on a 100° C. hot plate for about 5 min. The dielectric was cured in an $N_2$ glovebox environment for at least 2 hours at a temperature of 240-250° C. The final dielectric thickness measured by profilometry was 30-40 nm for a total dielectric thickness ($SiO_2$+BCB) of 330-340 nm.

Blend solutions were made by blending pristine solutions of the same concentration by the appropriate wt. %.

The blend concentration in chlorobenzene was 5 $mg^{-1}$ mL with respect to the total additive +polymer semiconductor content. For blade-coating, a blade-coater was built using a LTA-HS actuator and integrated CONEX-CC controller with the substrate set upon a hot plate. The blades used were glass microscope slides, which were cleaned by piranha solution. The substrate was coated by injecting 8 μL of solution in between a ≈100 μm channel formed between the blade and the substrate. The blade angle was set to 60° relative to the plane of the substrate. Blade-coating conditions were 100° C. and 1.2 mm $s^{-1}$. The solutions were prepared neat and mixed by volume to obtain the correct blend ratios.

For top contact devices, OFET active layers (pristine and blend layers) were spin-coated at 1500 revolutions per minute (RPM) (for devices measured in FIGS. 4(g), 4(h), 5(a)-5(c) and 6) or 2000 RPM (for devices measured in FIGS. 4(a)-4(f), 7(a)-7(d), 9(b)-9(c), 10(a)-10(b) and 11) onto the BCB (30-50 nm)/$SiO_2$ (300 nm) substrates.

Silver source-drain contacts (80 nm thick) were thermally evaporated through a shadow mask to obtain channel lengths ranging between 80-200 μm and channel widths of 2.5 mm. The final architecture is doped Si/$SiO_2$ (300 nm)/BCB (50 nm)/blend layer/Ag (80 nm). For bottom contact devices, source and drain contacts (50 nm Au on 5 nm Ni) were deposited by a photolithography process and electron-beam deposition. Acid hydrolysis was used to etch the Ni underlayer and to activate the surface. The substrates were passivated by 0.2% dodecyltrichlorosilane in toluene for at 80° C. for 25 minutes after treatment with $UVO_3$, followed by sample deposition under nitrogen. OFET active layers were spin-coated or blade-coated onto these substrates. The final architecture is doped Si/DTS-treated $SiO_2$ (300 nm)/Au (50 nm)/blend layer.

Samples were annealed at 200° C. for 8 minutes before measurement or as otherwise specified. For the devices labeled as "2LD", the two-layer deposition was performed by spin-coating "on-the-fly" at 2000 RPM.

Figure 8B:
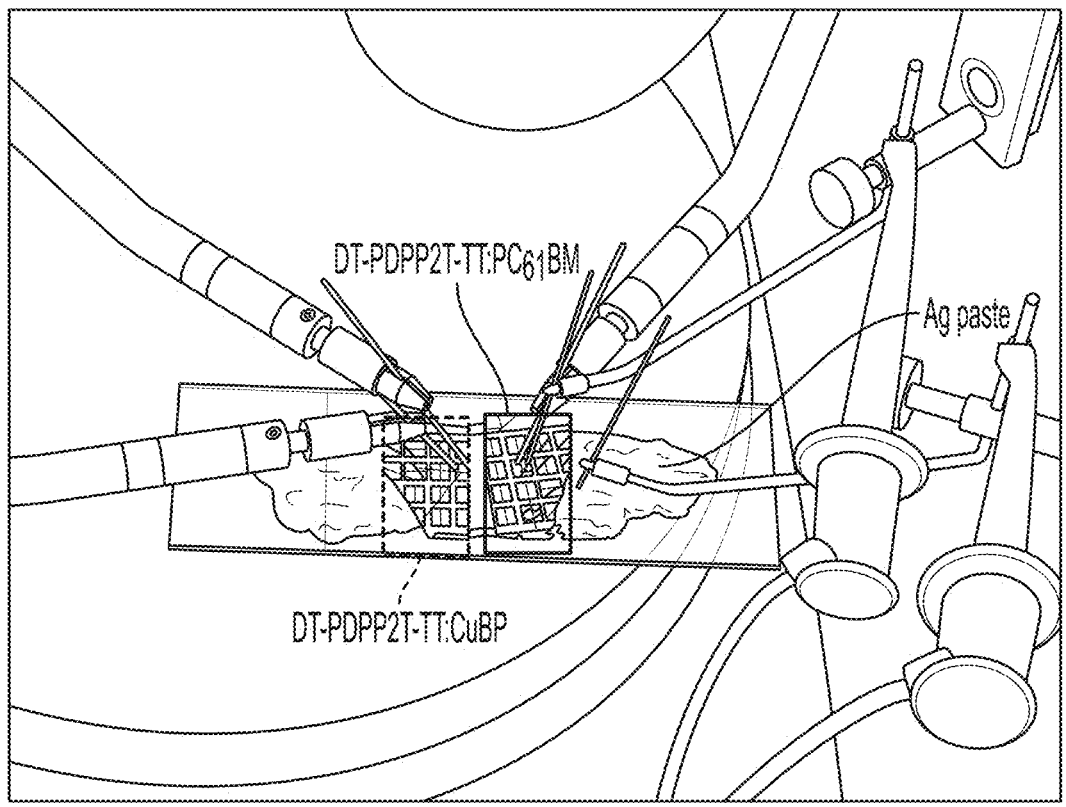

Inverters were fabricated by connecting an n-OFET and a p-OFET in accordance with an inverter circuit diagram. A photograph of the inverter measurement setup is shown in the FIG. 8(b). Inverter characteristics were measured by applying a constant supply voltage and sweeping the input voltage while measuring the output voltage. The gain was calculated by measuring the slope of the inverter characteristics. The least square method, which takes the largest square that can fit in between the inverted transfer curve and the regular transfer curve, was used to calculate the noise margins.

b. Testing

The mobility of blend devices were obtained by fitting the following equation to the saturation regime transfer characteristics (linear relationship between the square root of the current and the voltage):

$$I_D = \frac{W \times C_i}{2L} \mu_{FET}(V_G - V_T)^2 \qquad (1)$$

where W is the channel width (2.5 mm), L is the channel length (160 μm), $C_i$ is the gate dielectric layer capacitance per unit area (9.6 nF $cm^{-2}$), $V_G$ is the gate voltage, $V_T$ is the threshold voltage, $I_D$ is the source-drain voltage, and $\mu_{FET}$=OFET mobility.

Devices were measured under nitrogen in a glovebox using a Signatone 1160 probe station and Keithley 4200 semiconductor parametric analyzer. Mobility values are calculated in a gate voltage range of 30 to 50 V at a source-drain voltage of 80 V for n-channel OFET.

c. Complementary Inverter as a Simple Voltage Divider

It has been shown that a complementary inverter can be simplified and modeled as a simple voltage divider (where each OFET acts as a resistor) to give the relationship $$V_{out} = V_{dd} \frac{R_2}{R_1 + R_2}$$

with $R_1$ and $R_2$ as the resistors and $V_{out}$ as the voltage drop between the resistors. Ignoring contact resistance and contributions from $V_T$, the inverter characteristics can be simulated as:

$$V_{out} = V_{in} + \sqrt{(V_{dd} - V_{in})^2 \frac{\mu_p^{pFET}}{\mu_p^{pFET} + \mu_p^{nFET}} - V_{in}^2 \frac{\mu_n^{nFET}}{\mu_p^{pFET} + \mu_p^{nFET}}} \quad \text{when } V_{in} < V_{dd}/2$$

and $$V_{out} =$$

$$V_{in} - \sqrt{V_{in}^2 \frac{\mu_n^{nFET}}{\mu_n^{nFET} + \mu_n^{pFET}} - (V_{dd} - V_{in})^2 V_{in}^2 \frac{\mu_p^{pFET}}{\mu_n^{nFET} + \mu_n^{pFET}}} \quad \text{when } V_{in} > V_{dd}/2.^1$$

In the simulation described herein (FIG. 9(a)), $V_{dd}$ is the power supply voltage set to 60 V and $\mu_p^{pFET}$ (p-type type mobility of the p-type transistor)=$\mu_n^{nFET}$ (n-type mobility of the n-type transistor)=1 cm$^2$ V$^{-1}$ s$^{-1}$. The values of $\mu_n^{pFET}$ and $\mu_p^{nFET}$ are set to equal each other and are modulated to generate the voltage transfer curves shown in the main text.

d. Inverter Characteristics

Inverters were fabricated by connecting p- and n-FET gates.

Inverter characteristics were measured by applying a constant supply voltage and sweeping the input voltage while measuring the output voltage. The gain was calculated by measuring the slope of the inverter characteristics. The least square method, which takes the largest square that can fit in between the inverted transfer curve and the regular transfer curve, was used to calculate the noise margins.

Inverters with the highest gain were measured at $|V_{dd}|=60$ V with a voltage step of 0.05 V and the slope of multiple points was used to calculate the gain. These measurements resulted in gain values of typically 150-200. Measuring at other values of $V_{dd}$ and at different voltage step can result in different gain values (an example has been shown here, but all inverters displayed gain >10, which is considered necessary for practical applications).

e. Bias Stress Test

Bias stress tests involved applying $V_g$=−60 V for circa (ca.) 10 seconds (s) before immediately switching to forward and reverse sweep $V_g$ from 0 to 60 V. Trapped holes may be expected to result in an apparent gate threshold shift; therefore, a large −$V_g$ would cause accumulation of charge carriers and a shift in threshold voltage. As shown in the present disclosure, a shift in threshold voltage is observed for the DT-PDPP2T-TT blend OFET; however, the results are similar for the pristine ambipolar OFET. While a slightly larger shift in threshold voltage is observed for the blend after the stressing measurement, trapping in DT-PDPP2T-TT complicates the analysis of trapping in the blend.

Process Steps

Figure 13:
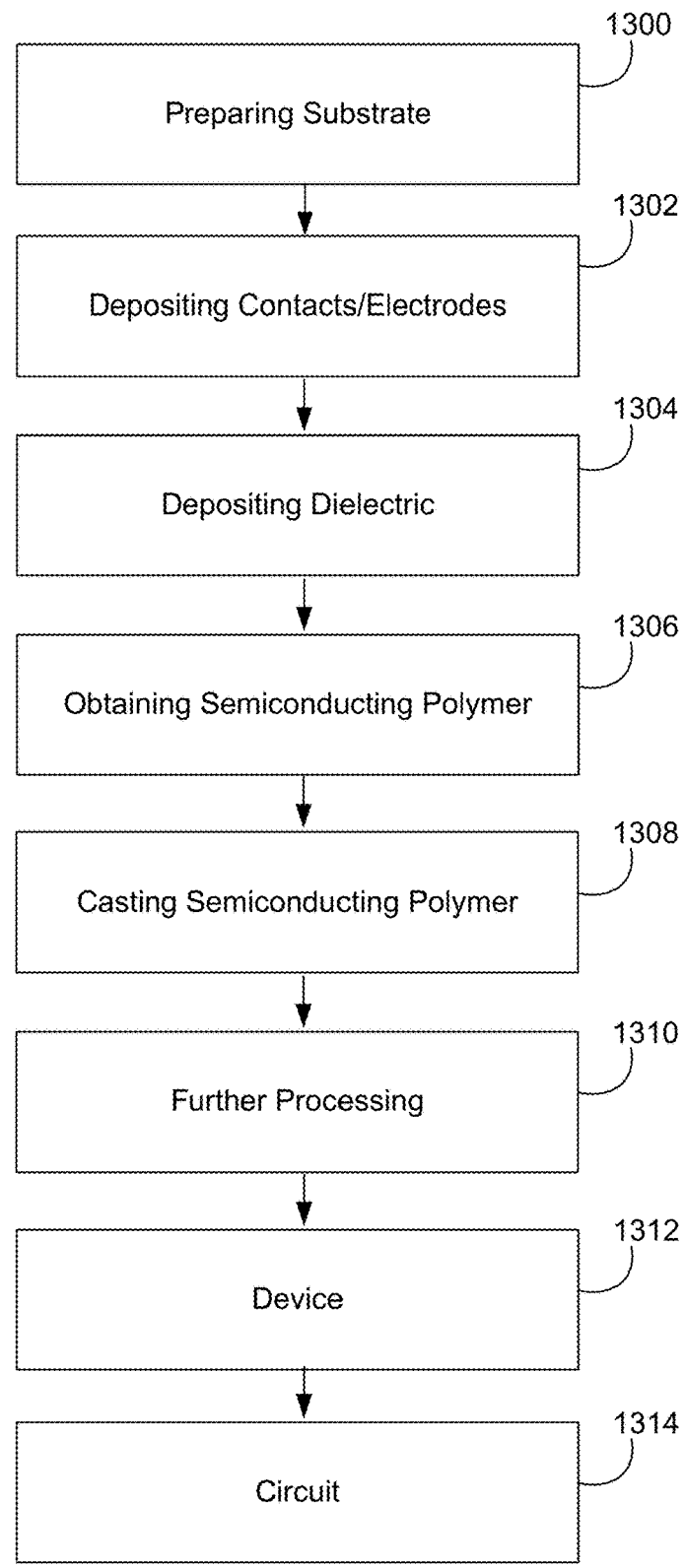
FIG. 13 is a flowchart illustrating a method of fabricating a device according to one or more embodiments.

FIG. 13 is a flowchart illustrating a method for fabricating a film or device such as an OFET. The method can comprise the following steps.

Block 1300 represents obtaining/providing and/or preparing a substrate. In one or more embodiments, the substrate comprises a flexible substrate. Examples of a flexible substrate include, but are not limited to, a plastic substrate, a polymer substrate, a metal substrate, or a glass substrate. In one or more embodiments, the flexible substrate is at least one film or foil selected from a polyimide film, a polyether ether ketone (PEEK) film, a polyethylene terephthalate (PET) film, a polyethylene naphthalate (PEN) film, a polytetrafluoroethylene (PTFE) film, a polyester film, a metal foil, a flexible glass film, and a hybrid glass film. In one or more embodiments, the substrate is a swellable substrate.

Block 1302 represents optionally forming/depositing contacts or electrodes (e.g., p-type, n-type contacts, a gate, a source, and/or drain contacts) on or above (or as part of) the substrate.

In an OFET embodiment comprising a top gate & bottom contact geometry, source and drain contacts are deposited on the substrate. Examples of materials for the source and drain contacts include, but are not limited to, gold, silver, silver oxide, nickel, nickel oxide (NiOx), molybdenum, and/or molybdenum oxide. In one or more embodiments, the source and drain contacts of the OFET further comprise a metal oxide electron blocking layer, wherein the metal in the metal oxide includes, but is not limited to, nickel, silver, or molybdenum.

In an OFET embodiment comprising a bottom gate geometry, a gate electrode is deposited on the substrate. In one or more embodiments, the gate contact (gate electrode) is a thin metal layer. Examples of the metal layer for the gate include, but are not limited to, an aluminum layer, a copper layer, a silver layer, a silver paste layer, a gold layer or a Ni/Au bilayer. Examples of the gate contact further include, but are not limited to, a thin Indium Tin Oxide (ITO) layer, a thin fluorine doped tin oxide (FTO) layer, a thin graphene layer, a thin graphite layer, or a thin PEDOT:PSS layer. In one or more embodiments, the thickness of the gate electrode is adjusted (e.g., made sufficiently thin) depending on the flexibility requirement.

The gate, source, and drain contacts can be printed, thermally evaporated, or sputtered, for example.

Block 1304 represents optionally depositing a dielectric on the gate electrode, e.g., when fabricating an OFET in a bottom gate configuration. In this example, the dielectric is deposited on the gate contact's surface to form a gate dielectric and a gate connection on the dielectric.

Examples of depositing the dielectric include forming a coating including one or one or more dielectric layers on the substrate (and selecting a thickness of the dielectric layers or coating). In one or more examples, the dielectric is structured or patterned, e.g., to form nanogrooves or nanostructures in the dielectric. Examples of dimensions for the nanogrooves include, but are not limited to, a nanogroove depth of 6 nanometers or less and/or a nanogroove width of 100 nm or less.

Examples of dielectric layers include, but are not limited to, a single polymer (e.g., PVP) dielectric layer or multiple dielectric layers (e.g., bilayer dielectric). A single polymer dielectric layer may be preferred in some embodiments (for easier processing, or for more flexibility). In one embodiment, the dielectric layer comprises silicon dioxide (SiO$_2$). In another embodiment, the dielectric layers form a polymer/SiO$_2$ bilayer. In yet another embodiment, the dielectric layers form a polymer dielectric/SiO$_2$/SAM multilayer with the SiO$_2$ on the polymer and the alkylsilane or arylsilane Self Assembled Monolayer (SAM) layer on SiO$_2$. In yet a further embodiment, the dielectric layers form a SiO$_2$/SAM bilayer with the alkylsilane or arylsilane SAM layer on the SiO$_2$. Various functional groups may be attached to the end of the alkyl groups to modify the surface property of the SAM layer.

The thickness of the SiO$_2$ may be adjusted (e.g., made sufficiently thin) depending on the composition of the dielectric layers and the flexibility requirement. For example, in one embodiment, the dielectric layer might not include a polymer dielectric layer and still be flexible.

In one or more embodiments, the nanogrooves/nanostructures are formed/patterned using nano imprint lithography. In one example, patterning the dielectric layers comprises nano-imprinting a first dielectric layer (e.g., PVP) deposited on a gate metal surface of the substrate; and depositing a second dielectric layer on the nanoimprinted first dielectric layer, wherein a thickness of the second dielectric layer (e.g., comprising $SiO_2$) is adjusted.

Block 1306 represents obtaining/fabricating one or more semiconducting polymers and one or more hole trapping compounds (e.g., n-type dopants), and combining the semiconducting polymer(s) with the hole trapping molecule/compound(s).

In one or more examples, the combining comprises forming a solution comprising a weight $W_{HT}$ of the hole trapping compound(s) and a weight $W_{CP}$ of the donor-acceptor semiconducting polymer(s), wherein a total weight percentage (wt. %) of the hole trapping compounds in the solution is in a range of 0.005-50 wt. % (e.g., 0.005-10 wt. %) based on a total weight of the solution (i.e., wt. %=$[W_{HT}/(W_{HT}+W_{CP}+$Weight of solvent$)]\times 100$. For example, if the polymer concentration is 5 mg/ml (roughly about 0.5 wt. %), the additive to polymer ratio is from 1:99 to 95:5 (corresponding to about 0.005-10 wt. % of the total solution).

In other examples, the weight ratio of hole trapping compound to the polymer in the solution is in a range of 1:99 wt. % (e.g., 0.05 mg of hole trapping compound and 4.95 mg polymer if the solution concentration is 5 mg/ml) to 95:5 wt. % hole trapping compoound:polymer.

In other examples, a weight $W_{CP}$ of the semiconducting polymer(s) added in the solution and a weight $W_{HT}$ of the hole trapping compound(s) added in the solution are such that $W_{CP}$ is in a range of 5%-99% or 1%-99% of the total weight of the solution including the semiconducting polymers, the hole trapping compound, and the solvent. In yet further examples, a total weight ($W_{CP}$) of the donor-acceptor copolymers added in the solution and a total weight $W_{HT}$ of the hole trapping compounds added in the solution are such that $[W_{CP}/(W_{CP}+W_{HT})]\times 100$ is in a range of 5%-99%.

Examples of the hole trapping molecule/compound include any chemical entity that traps/accepts holes transferred to it from another compound or injected to it from an electrode. The hole transfer process can be either reversible or irreversible. The hole trapping/accepting molecule/compound can be an organic, inorganic or hybrid semiconductor. When the hole transfer is from a hole donor/ambipolar semiconducting polymer to the hole accepting compound, the HOMO energy level of the hole accepting compound shall be higher than the HOMO energy level of the hole donor/ambipolar semiconducting polymer. The holes accepted by the hole acceptor or hole accepting molecule/compound can be in their ground state or excited state.

Further examples of hole trapping molecule/compounds include, but are not limited to, Tetrathiafulvalene (TTF) and its derivatives, 1H-benzoimidazole (DMBI) and its derivatives, Decamethylcobaltocene (DMC) and its derivatives, tetrabenzoporphyrin (BP or TBP) and its derivatives, copper tetrabenzoporphyrin (CuBP) and its derivatives, bicyclo[2,2,2]-octadiene-fused porphyrins, tetraethano-tetrabenzoporphyrin (CP, BP precursor) and its derivatives, copper tetraethano-tetrabenzoporphyrin (CuCP, CuBP precursor) and its derivatives, Spiro-MeOTAD and its derivatives.

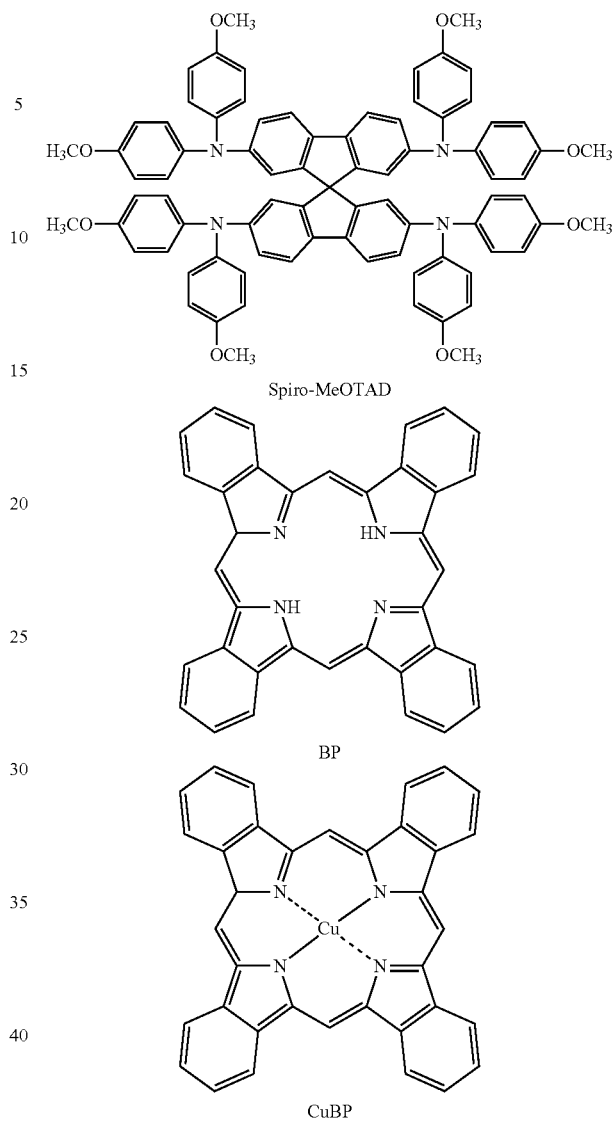

Spiro-MeOTAD

BP

CuBP

The mechanism of increasing stability of the thin film transistor using a hole-accepting molecule should be applicable to any type of polymer. For example, the semiconducting polymer can comprise a copolymer with donor and acceptor repeating units having the structure $[D-A]_n$ or $[D-A-D-A]_n$ wherein D comprises the donor, A comprises the acceptor, and n is an integer representing the number of repeating units. In one or more embodiments, the structure has a regioregular conjugated main chain section having n=5-150, or more, contiguous repeat units. In some embodiments, the number of repeat units n is in the range of 10-40 repeats. The regioregularity of the conjugated main chain section can be 95% or greater, for example.

In one or more examples, the semiconductor polymer is an ambipolar polymer capable of conducting both holes and electrons (e.g., a copolymer with donor and acceptor repeating units). Many low bandgap donor-acceptor copolymers show ambipolar charge conduction due to their low-lying LUMO and high-lying HOMO levels. Further information on the donor and acceptor structures can be found in the 579' application cross-referenced above.

In one or more embodiments, the donor-acceptor polymers each comprise a DPP unit or a unit having a structure

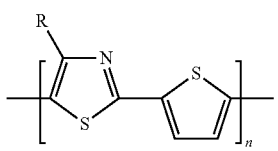

In one or more further embodiments, the donor-acceptor semiconducting polymer(s) each comprise a conjugated main chain section, said conjugated main chain section having a repeat unit that comprises a pyridine of the structure:

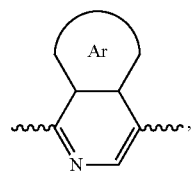

wherein Ar is a substituted or non-substituted aromatic functional group, or Ar is nothing and the valence of the pyridine ring is completed with hydrogen. In one or more examples, the pyridine is regioregularly arranged along the conjugated main chain section.

Examples of the pyridine unit include, but are not limited to:

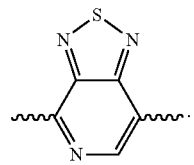

In one or more examples, the repeat unit further comprises a dithiophene of the structure:

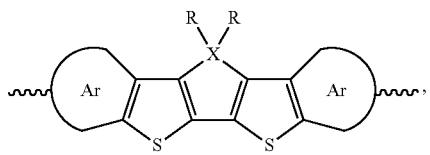

wherein each Ar is independently a substituted or non-substituted aromatic functional group, or each Ar is independently nothing and the valence of its respective thiophene ring is completed with hydrogen, each R is independently hydrogen or a substituted or non-substituted alkyl, aryl or alkoxy chain; and X is C, Si, Ge, N or P. In the dithiophene, the R comprising the substituted or non-substituted alkyl, aryl or alkoxy chain can be a $C_6$-$C_{30}$ substituted or non-substituted alkyl or alkoxy chain, —$(CH_2CH_2O)_n$ (n=2~20), $C_6H_5$, —$C_nF_{(2n+1)}$ (n=2~20), —$(CH_2)_nN(CH_3)_3Br$ (n=2~20), 2-ethylhexyl, $PhC_mH_{2m+1}$ (m=1-20), —$(CH_2)_nN(C_2H_5)_2$ (n=2~20), —$(CH_2)_nSi(C_mH_{2m+1})_3$ (m, n=1 to 20), or —$(CH_2)_nSi(OSi(C_mH_{2m+1})_3)_x(C_pH_{2p+1})_y$ (m, n, p=1 to 20, x+y=3). In some embodiments, the R groups in the dithiophene are the same, in other embodiments, the R groups in the dithiophene are different.

Examples of dithiophene units include those illustrated in FIGS. 6b-6d of U.S. patent application Ser. No. 15/349,908 entitled "FLUORINE SUBSTITUTION INFLUENCE ON BENZO[2,1,3]THIODIAZOLE BASED POLYMERS FOR FIELD-EFFECT TRANSISTOR APPLICATIONS," and Table B (FIG. 30B) in U.S. Utility patent application Ser. No. 14/426,467, filed on Mar. 6, 2015, by Hsing-Rong Tseng, Lei Ying, Ben B. Y. Hsu, Christopher J. Takacs, and Guillermo C. Bazan, entitled "FIELD-EFFECT TRANSISTORS BASED ON MACROSCOPICALLY ORIENTED POLYMERS", both of which applications are incorporated by reference herein and cross-referenced above.

In one or more examples, the dithiophene unit comprises:

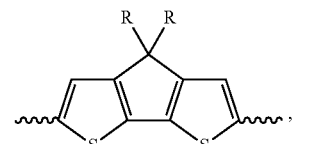

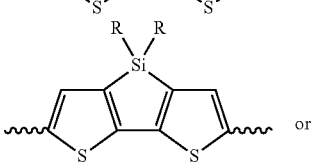

or

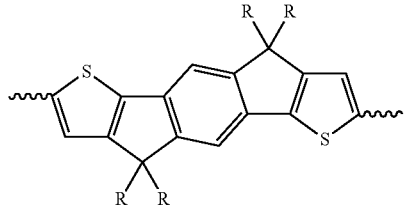

where R is as described above.

In one or more embodiments, combination of the pyridine (acceptor) and the dithiophene (donor) yields the donor-acceptor copolymer of the formula:

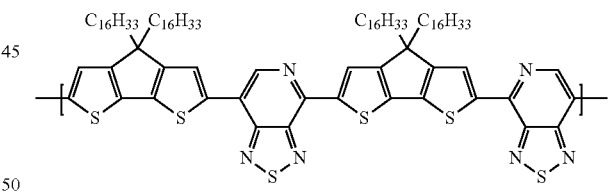

In other examples, the $C_{16}H_{33}$ are replaced with R groups as discussed above.

In one or more further examples, the semiconducting polymer comprises polymer chains having a backbone including an aromatic ring, the aromatic ring comprising a side group (e.g., Fluorine) which may have reduced susceptibility to oxidization as compared to a pyridine ring. Thus, the semiconducting polymer can have fluoro functionality such as an acceptor structure including a regioregular fluorophenyl unit.

In one or more examples comprising fluorinated conjugated polymer chains, each of the donor-acceptor semiconducting polymers comprise a conjugated main chain section having a repeat unit that comprises a compound of the structure:

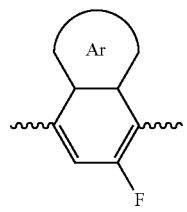

wherein Ar is a substituted or non-substituted aromatic functional group, or Ar is nothing and the valence of the ring comprising fluorine (F) is completed with hydrogen. In one or more examples, the ring comprising F is regioregularly arranged along the conjugated main chain section.

In one or more examples, the ring comprising the fluorine has the structure:

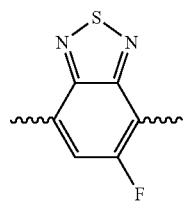

Other examples include those illustrated in FIG. 6a of U.S. patent application Ser. No. 15/349,908 entitled "FLUORINE SUBSTITUTION INFLUENCE ON BENZO[2,1,3] THIODIAZOLE BASED POLYMERS FOR FIELD-EFFECT TRANSISTOR APPLICATIONS," (which application is incorporated by reference herein and cross-referenced above) where each R is independently a substituted or non-substituted alkyl chain, which can be a $C_6$-$C_{30}$ substituted or non-substituted alkyl chain, —$(CH_2CH_2O)_n$ (n=2~20), $C_6H_5$, —$C_nF_{(2n+1)}$ (n=2~20), —$(CH_2)_nN(CH_3)_3$ Br (n=2~20), —$(CH_2)_nN(C_2H_5)_2$ (n=2~20), 2-ethylhexyl, $PhC_mH_{2m+1}$ (m=1-20), —$(CH_2)_nSi(C_mH_{2m+1})_3$ (m, n=1 to 20), or —$(CH_2)_nSi(C_mH_{2m+1})_3)_x(C_pH_{2p+1})_y$ (m, n, p=1 to 20, x+y=3), for example; in some embodiments, the R groups attached to the ring comprising F are the same, in other embodiments the R groups attached to the ring comprising F are different.

In one or more embodiments, the repeat unit comprising the fluorinated acceptor further comprises a dithiophene as the donor and as described previously.

Thus, in one or more embodiments, the semiconducting polymer is a regioregular semiconducting polymer comprising a repeating unit of the structure:

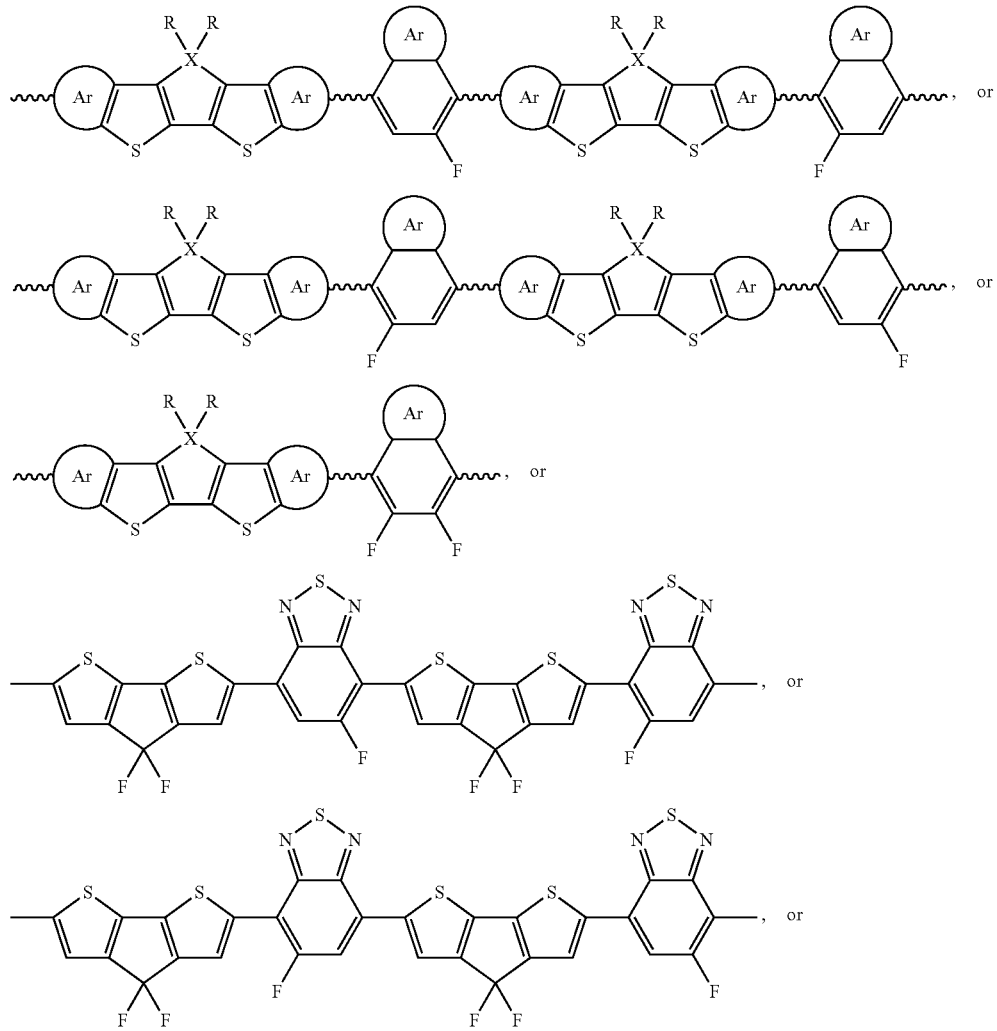

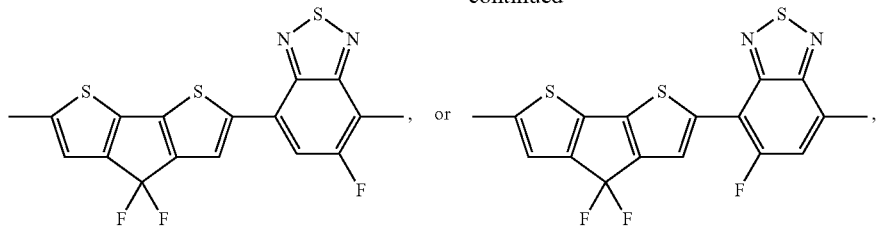

where the ring comprising F is regioregularly arranged along the conjugated main chain section pointing toward the direction shown in the structures above, Ar is a substituted or non-substituted aromatic functional group containing one, two, three or more aromatic rings, or Ar is nothing and the valence of the ring comprising fluorine (F) or the valence of the dithiophene is completed with hydrogen, the R groups comprising the substituted or non-substituted alkyl, aryl or alkoxy chain can be a $C_6$-$C_{30}$ substituted or non-substituted alkyl or alkoxy chain, —$(CH_2CH_2O)_n$ (n=2~20), $C_6H_5$, —$C_nF_{(2n+1)}$ (n=2~20), —$(CH_2)_nN(CH_3)_3Br$ (n=2~20), 2-ethylhexyl, $PhC_mH_{2m+1}$(m=1-20), —$(CH_2)_nN(C_2H_5)_2$ (n=2~20), —$(CH_2)_nSi(C_mH_{2m+1})_3$ (m, n=1 to 20), or —$(CH_2)_nSi(OSi(C_mH_{2m+1})_3)_x(C_pH_{2p+1})_y$ (m, n, p=1 to 20, x+y=3).

For example, the semiconducting polymer can be regioregular poly[5-fluoro-[2,1,3]benzothiadiazole-4,7-diyl(4,4-dihexadecyl-4H-cyclopenta[2,1-b:3,4-b']dithiophene-2,6-diyl)-5-fluoro-[2,1,3]benzothiadiazole-7,4-diyl(4,4-dihexadecyl-4H-cyclopenta[2,1-b:3,4-b']dithiophene-2,6-diyl)] (P2F or PCDTFBT).

Further examples of the fluorophenylene unit include at least one fluorophenylene unit selected from:

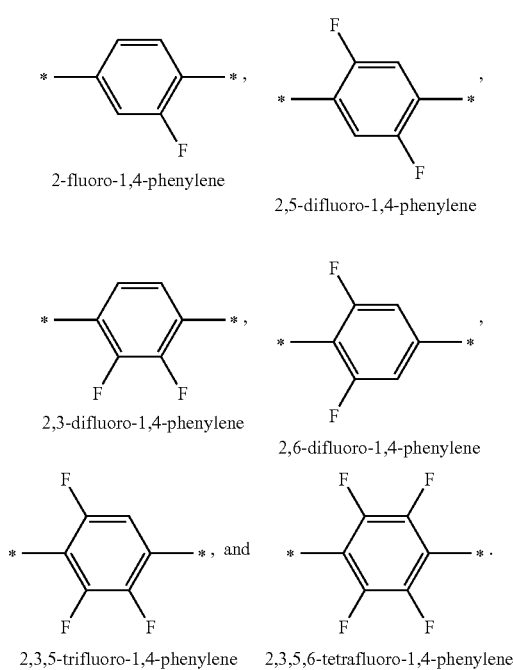

Further information and examples are found in U.S. Utility patent application Ser. No. 15/496,826, filed Apr. 25, 2017, by Guillermo Bazan and Ming Wang, entitled "NOVEL WEAK DONOR-ACCEPTOR CONJUGATED COPOLYMERS FOR FIELD-EFFECT TRANSISTOR APPLICATIONS", which application claims the benefit under 35 U.S.C. Section 119(e) of U.S. Provisional Patent Application No. 62/327,311, filed Apr. 25, 2016, by Guillermo C. Bazan and Ming Wang, entitled "NOVEL WEAK DONOR-ACCEPTOR CONJUGATED COPOLYMERS FOR FIELD-EFFECT TRANSISTOR APPLICATIONS"; and U.S. Provisional Patent Application No. 62/489,303, filed Apr. 24, 2017, by Guillermo C. Bazan and Ming Wang, entitled "LINEAR CONJUGATED POLYMER BACKBONES IMPROVE THE ANISOTROPIC MORPHOLOGY IN NANOGROOVE ASSISTED ALIGNMENT ORGANIC FIELD-EFFECT TRANSISTOR APPLICATIONS", both of which applications are incorporated by reference herein.

Other examples include those described and fabricated according to the compositions and methods described in U.S. Utility patent application Ser. No. 15/349,920, filed Nov. 11, 2016, by Byoung Hoon Lee, Ben B. Y. Hsu, Chan Luo, Ming Wang, Guillermo Bazan, and Alan J. Heeger, entitled "SEMICONDUCTING POLYMERS WITH MOBILITY APPROACHING ONE HUNDRED SQUARE CENTIMETERS PER VOLT PER SECOND", which application claims the benefit under 35 U.S.C. Section 119(e) of U.S. Provisional Patent Application No. 62/253,975, filed Nov. 11, 2015, by Ming Wang and Guillermo Bazan, entitled "FLUORINE SUBSTITUTION INFLUENCE ON BENZO[2,1,3]THIODIAZOLE BASED POLYMERS FOR FIELD-EFFECT TRANSISTOR APPLICATIONS"; and U.S. Provisional Patent Application No. 62/263,058, filed Dec. 4, 2015, by Byoung Hoon Lee, Ben B. Y. Hsu, Chan Luo, Ming Wang, Guillermo Bazan, and Alan J. Heeger, entitled "SEMICONDUCTING POLYMERS WITH MOBILITY APPROACHING ONE HUNDRED SQUARE CENTIMETERS PER VOLT PER SECOND," (see e.g., FIG. 6 and FIG. 7 and related text of U.S. Provisional Application No. 62/263,058), all of which applications are incorporated by reference herein.

Yet further examples are fabricated following the method(s) described in U.S. Utility patent application Ser. No. 15/349,908, filed Nov. 11, 2016, by Ming Wang and Guillermo Bazan, entitled "FLUORINE SUBSTITUTION INFLUENCE ON BENZO[2,1,3]THIODIAZOLE BASED POLYMERS FOR FIELD-EFFECT TRANSISTOR APPLICATIONS", which application claims the benefit under 35 U.S.C. Section 119(e) of U.S. Provisional Patent Application No. 62/253,975, filed Nov. 11, 2015, by Ming Wang and Guillermo Bazan, entitled "FLUORINE SUBSTITUTION INFLUENCE ON BENZO[2,1,3]THIODIAZOLE BASED POLYMERS FOR FIELD-EFFECT TRANSISTOR APPLICATIONS", both of which applications are incorporated by reference herein.

The semiconductor polymers that can be combined with the hole accepting compounds are not limited to those described above. Other semiconducting polymers known in the art can be used (e.g., including semiconducting polymers described in the references cited in the references section).

In yet further examples, the semiconducting polymers comprise acceptor units chosen from the following:

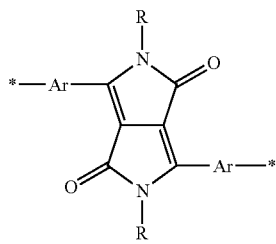

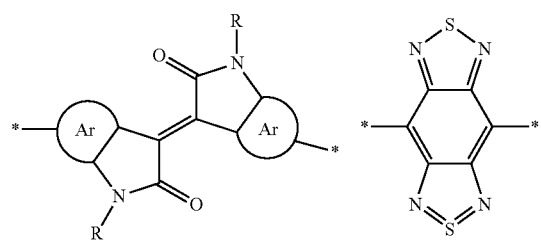

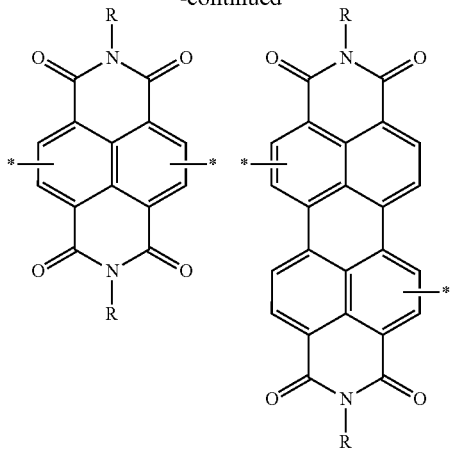

wherein each Ar is independently a substituted or non-substituted aromatic functional group, or each Ar is independently nothing and the valence is completed with hydrogen, each R is independently hydrogen or a substituted or non-substituted alkyl, aryl or alkoxy chain.

Block 1308 represents solution casting/processing a solution comprising the semiconducting copolymer(s) and the hole trapping compound (e.g., onto the dielectric) to form a film comprising the semiconducting copolymer(s) and the hole trapping compound.

In various embodiments, the solution casting further comprises casting/processing some additional donor-acceptor copolymers combined with electron acceptor compounds, the electron acceptor compounds accepting electrons and reducing electron current in the additional donor-acceptor copolymers as described in the 579' application. Examples of electron acceptor compounds include, but are not limited to:

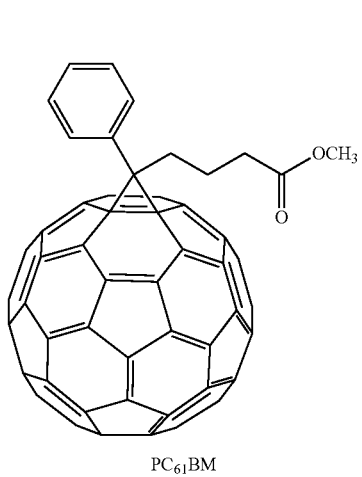

PC$_{61}$BM

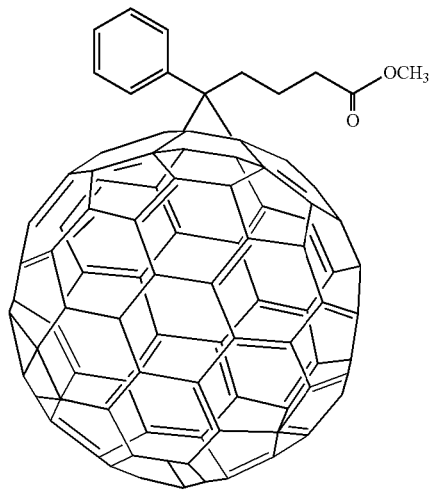

PC$_{85}$BM

-continued
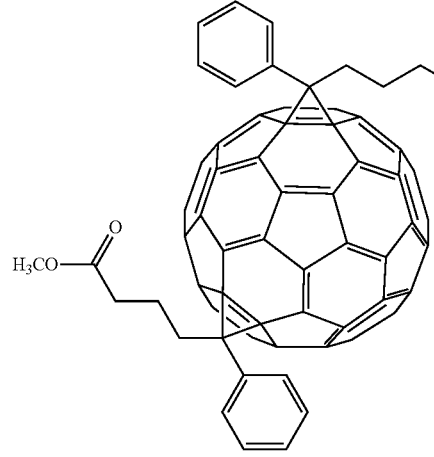
bis-PC₆₁BM
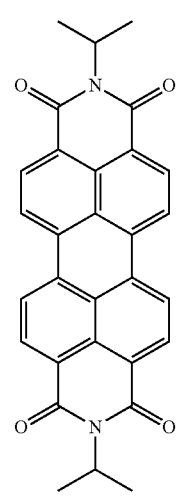
PDI-ST1
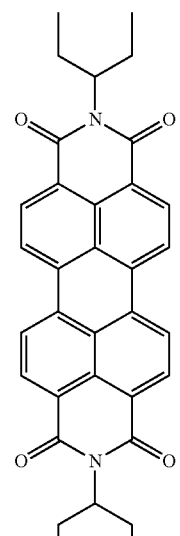
PDI-ST2
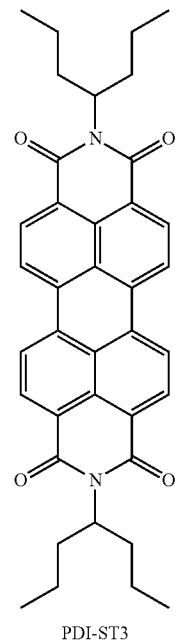
PDI-ST3
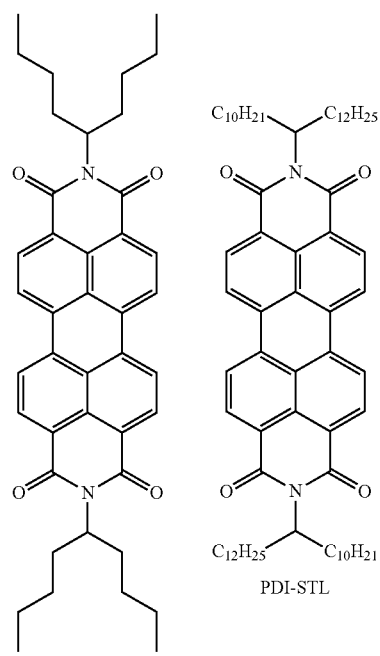
PDI-ST4
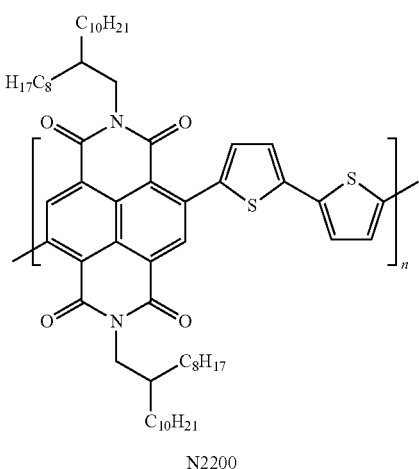
PDI-STL
N2200

-continued

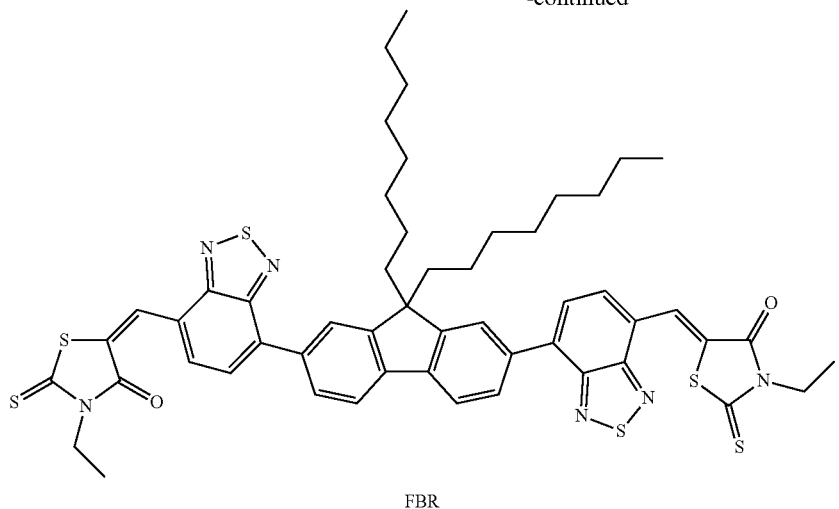

FBR

In this way, a film comprising both the n-type material (with hole trapping compound) and the p-type material (with electron accepting compound) in different regions may be constructed. In one or more examples, the donor-acceptor copolymers combined with the hole trapping compound have the same composition as the additional donor-acceptor copolymers combined with the electron accepting compounds (e.g., both comprising a backbone including the repeat unit including the same donor and the same acceptor).

Solution casting methods include, but are not limited to, inkjet printing, bar coating, spin coating, blade coating, spray coating, roll coating, dip coating, free span coating, dye coating, screen printing, and drop casting.

Nanogrooves can provide nucleation sites for growth of the polymer chains within the solution so that one or more of the polymer chains seed and stack within one or more of the nanogrooves.

The semiconducting polymer(s) and the hole trapping compound(s) are typically phase separated in the film (for example, the hole accepting/trapping compound is typically not formed in a continuous phase with the semiconducting polymer, and may comprise isolating regions, so that the hole trapping/accepting compound(s) only accept holes and do not substantially transport the holes in the active region of the device). However, the semiconducting polymer(s) can include a plurality of interconnected polymer chains.

Block 1310 represents further processing the polymer film cast on the patterned dielectric layers and/or the substrate. The step can comprise annealing/curing the film or allowing the film to dry. The step can comprise depositing source and drain contacts as described above, if necessary forming one or more source contact(s) and one or more drain contact(s) to the film comprising the donor-acceptor semiconducting polymers combined with the hole trapping compound and/or the donor-acceptor semiconducting polymer(s) combined with the electron accepting compound(s).

Block 1312 represents the end result, a device or film useful as a current transport region in a device.

Figure 14:
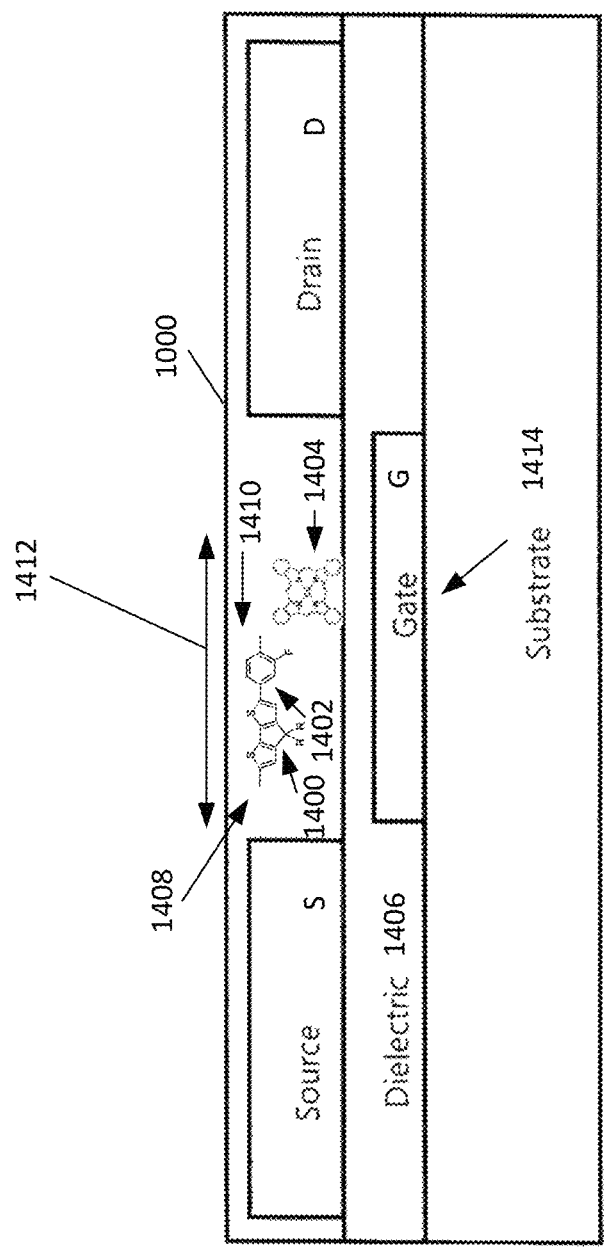
FIG. 14 illustrates an OFET comprising an active region including the compositions of matter according to one or more embodiments of the invention.

FIG. 14 illustrates an OFET comprising a source contact S and a drain contact D to a film 1400 comprising the semiconducting polymer(s) (donor-acceptor copolymer 1402) combined with the hole trapping compound(s) 1404; and a gate G on a dielectric 1406 so that the dielectric 1406 is between the gate G and the film 1400. The gate G applies a field to the semiconducting polymer 1402 across the dielectric 1406 to modulate conduction along the semiconducting polymer 1402 in a channel or current transport region between the source contact S and the drain contact D, thereby switching the OFET on or off FIG. 14 further illustrates the (e.g., aligned) donor-acceptor copolymers 1402 each comprising a main chain section 1408, the main chain section 1408 having a repeat unit 1410 that comprises at least one donor D and at least one acceptor A (e.g., as described in Block 1306).

In one or more examples, the OFET comprises means (e.g., grooves, nanogrooves or statutory equivalents thereof) for aligning the main chain axes 1412 of the polymer 1402 to the channel. The nanogrooves can orient/align the polymer chains 1408 so that polymer chains 1408 each have their backbone substantially parallel to a longitudinal axis of at least one of the nanogrooves, and the conduction between the source contact S and the drain contact D is predominantly along the backbones/main chain axes 1412 substantially parallel to a longitudinal axis of at least one of the nanogrooves, although charge hopping between adjacent polymers in a fiber bundle is also possible. For example, the means can align the main chain axes to an imaginary line bounded by the source S and the drain D or the means can align the main chain axes 1412 to an alignment direction in the channel between Source S and Drain D. The source and drain can be positioned such that a minimum distance between the source contact and drain contact is substantially parallel to the longitudinal axis of the nanogrooves.

In one or more film embodiments, the film comprises the donor-acceptor copolymer chains stacked into one or more fibers. For example, one or more of the structures (e.g., nanogrooves) in the dielectric or substrate on which the film is deposited can contact and align/orient one or more of the fibers such that the fibers are continuously aligned with (and/or at least partially lie within) one or more of the structures (e.g., nanogrooves). The width of an individual fiber can be about 2-3 nm, and fibers on the nanostructured/nanogrooved substrate can form, or stack into, fiber bundles having a width of 50~100 nm (as compared to fiber bundles having a width between 30~40 nm when fabricated on a non-structured substrate). In one or more embodiments, the aligned conjugated polymer chains are stacked to form a crystalline structure, and the polymer chains are oriented with an orientational order parameter between 0.9 and 1. The main-chain axes of the polymer chains can be aligned along the long-axis of the fiber while π-π stacking of the polymer chains can be in a direction along the short-axis of the fiber.

In other embodiments, means for aligning the semiconducting polymers comprises a fabrication method, including, but not limited to, blade coating, dip coating, and bar coating (or statutory equivalents thereof) of the semiconducting polymers on dielectric 1406 or substrate 1414.

Embodiments of the present invention are not limited to the particular sequence of depositing the source, drain, and gate contacts. For example, OFETs according to one or more embodiments of the present invention can be fabricated in a bottom gate & top contact geometry, bottom gate & bottom contact geometry, top gate & bottom contact geometry, and top gate & top contact geometry[9].

In various embodiments, the source, drain, gate, and dielectric have one or more compositions, structures, or configurations, the semiconducting polymer has a structure (including regioregularity), acceptor composition, donor composition, wt. %, HOMO, stability, is disposed in a film having a crystallinity, quality, and morphology, the hole trapping compound has a composition and wt. %, and the OFET, polymers, and the hole trapping compound are fabricated/processed/combined under conditions described herein, such that:

ambipolar transport is switched to electron-only (n-type) transport and/or the hole current is reduced relative to electron current in the semiconducting donor-acceptor copolymer; and/or hole current between the source and the drain is reduced by at least a factor of 100 (e.g., reduced by a factor of 10-1000) with at most a factor of 10 reduction (e.g., less than a factor of 2 reduction) in electron current between the source and the drain, as compared to the OFET/film/current transport region comprising the pristine semiconducting polymer; and/or the OFET has an on/off ratio of at least 10, at least $10^2$, or at least $10^3$, the OFET has a mobility in a saturation regime of at least 1 $cm^2 V^{-1}s^{-1}$ or in a range of 1-50 $cm^2V^{-1}s^{-1}$, e.g., when the drain voltage Va is in a range of 10 V to 120 V; and/or so as to achieve a desired balance between mobility and on/off ratio of the OFETs; and/or the hole-accepting compound is effective as a current and/or threshold voltage stabilizing agent in the device; and/or the donor-acceptor copolymers and the hole trapping compounds are phase separated in a film, and the main chain axes of a plurality of the donor-acceptor copolymers are interconnected; and/or the hole trapping compounds/additives have a HOMO level that is higher in energy (closer to vacuum) than the HOMO level of the donor-acceptor semiconducting copolymers (e.g., in one or more examples, the ambipolar semiconducting polymers have a HOMO is in a range including, but not limited to, 5.5-5.5 eV); and/or a first portion of the donor-acceptor semiconducting copolymers are p-type doped and a second portion of the donor-acceptor semiconducting copolymers are combined with electron acceptor compounds/additives having a LUMO level lower than the LUMO level of the donor-acceptor semiconducting polymers (e.g., in one or more examples, the ambipolar semiconducting polymers have a LUMO is in a range including, but not limited to, 3.5-4.5 eV); and/or each of a plurality of the OFETs are characterized by an input bias voltage applied to the gate for switching into the OFET on (or into a binary state "1") that is stable (e.g., within 1% of the input bias voltage used for the other of the plurality of the OFETs and/or an input bias voltage that does not change by more than 1% after the bias voltage is applied multiple times), each of a plurality of the OFETs are characterized by an input bias voltage applied to the gate for switching the OFET off (or into a binary state "0") that is stable (e.g., within 1% of the input bias voltage used for the other of the plurality of the OFETs and/or a input bias voltage that does not change by more than 1% after the input bias voltage is applied multiple times), and each of the OFETS are characterized by an output voltage outputted from the each of the OFETs (in response to the input bias voltage) that is stable (e.g., within 1% of the output voltage from the other of the plurality of the OFETs in response to the same input bias voltage and/or an output voltage that does not change by more than 1% after the input bias voltage is applied multiple times).

Block 1314 represents the optional step of connecting one or more of the OFETs in an electronic circuit, e.g., as illustrated in FIGS. 8(a), 9(i) and 12(a-b). In one or more embodiments, the electronic circuit comprises a logic gate including, but not limited to, an inverter.

As described herein, one or more devices (e.g., n-type or n-channel OFETs) comprising one or more donor acceptor copolymers combined with one or more hole trapping compounds may be combined, on the same substrate, with devices (e.g., p-type or p-channel OFETs) comprising additional donor-acceptor copolymers combined with electron acceptor compounds as described herein and in the 579' application. In various examples, the n-type and p-type OFETs both comprise donor-acceptor copolymers having the same composition or backbone structure, share similar source, drain, and gate configurations, and/or comprise the same or substantially similar dielectric.

In one or more embodiments, a weight and composition of the hole trapping compounds in the first n-type OFET, weight(s) and composition(s) of the donor-acceptor copolymers in each of the first n-type OFET and the second p-type OFET, and a weight of and composition of the electron acceptor compounds in the second p-type OFET, are such that each of the OFETs have a mobility in a saturation regime of at least 1 $cm^2 V^{-1}s^{-1}$ and an ON/OFF ratio of at least 1000.

The n-type and p-type OFETs may both have substantially the same stability. For example, in one or more inverter examples wherein each inverter comprises the n-type OFET connected to the p-type OFET as illustrated in FIG. 8(a):

a bias voltage Vin applied in order to switch each inverter into a binary state "1"; a bias voltage Vin applied in order to switch each inverter into a binary state "0"; and a voltage Vout outputted from each of the inverters in order to indicate the binary state, are stable (e.g., within 1%) after multiple cycles of the inverter between the binary states, and/or the bias voltages required at each of the inputs Vin to the inverters are the same (e.g., to within 1%) for each inverter, and the voltages Vout outputted from each the inverters are the same (e.g., to within 1%) for each inverter; and/or the inverter has a gain of at least 100; and/or the inverter has a noise margin of at least 20 V (e.g., at least 67% of maximum); and/or the inverter does not draw power in an off state.

Advantages and Improvements

Organic semiconductors exhibit hole and electron mobilities[2-6] ($\mu$) that approach values relevant for commercial applications and offer certain advantages over their inorganic counterparts, including the possibility of solution deposition and access to a wide range of chemical structures that can be tailored to fulfill specific requirements.[7,8] Moreover, polymer-based organic field-effect transistors have potential applications in flexible and low-cost electronics including, but not limited to, light-emitting diodes, liquid-crystal displays, and various sensor applications. For many applications, both positive and negative charge transporting devices are necessary for logic circuits, and high-performance n-type polymer semiconductors are not as ubiquitous as the positive counterpart.

Examination of the literature reveals that many conjugated polymers used in OFETs exhibit ambipolar conduction.[9-13] To what extent n-type (electron) or p-type (hole) transport dominates depends not only on the intrinsic properties of the material itself, but also on the device architecture; for example, different electrodes can be used to manage charge injection barriers or the dielectric properties can be modified to inhibit interfacial trapping.[14-16] Dual injection and transport of both carriers, however, can result in transistor characteristics with turn-on voltages that depend on the drain voltage ($V_d$), and small $I_{ON}/I_{OFF}$ values, as defined by the minimum and maximum current for ambipolar OFETs.[17] In response to the opportunities and limitations offered by ambipolar semiconductors, recent efforts have focused on managing charge transport in order to fabricate high performance OFETs and complementary inverters. For example, contact doping has been used to achieve unipolar p-type OFETs.[18] In another report, dielectric surface modifications effectively truncated ambipolar conduction, and low-power complementary inverters were achieved.[19]

The present disclosure offers another route to manage transport in ambipolar semiconductors by introducing solution-processable charge-carrier traps, which can selectively disrupt either p- or n-type conduction in ambipolar polymers. In one example, a molecule that traps positive charge carriers (i.e., a hole trap) is introduced into the semiconducting polymer so as to eliminate or suppress the positive charge carriers and improving the performance of negative charge carrier (n-type) devices. In illustrative examples, an effective amount of the hole trapping compound may be controlled, administered to, and processed in solution with, an ambipolar organic semiconductor in order to control and/or obtain a desired n-type current (converting ambipolar transport of the ambipolar organic semiconductor to n-type transport), and/or threshold voltage stability of the OFET, and/or ON/OFF ratio, while reducing hole current between the source and the drain contact. In one or more of the best examples presented herein, hole current is reduced by ~4 orders of magnitude with only a factor of ~2 reduction in electron current. This is promising for the realization of solution-processable n-type polymer OFETs.

Relative to other methods that control ambipolar transport, the method presented herein does not require additional evaporation or substrate modification steps, is not limited to specific device architectures (including contacts and dielectric layer), and can be used to fabricate both p- and n-only OFETs on a single substrate. Indeed, blending of conjugated polymers and additives is a simple process that can be carried out with solution-processing methods and that can be extended to high throughput, practical fabrication technologies such as ink-jet printing.

Thus, by using the outlined methodology, complementary circuits can be fabricated from solution using an ambipolar polymer and a hole trap rather than having to synthesize new materials for n-type transport. The resulting complementary inverters based on blend OFETs display high gain and wide noise margins, and were superior in terms of reduced voltage losses relative to the pristine ambipolar polymer case. While functional organic circuits utilizing n- and p-type wide band-gap organic semiconductors have been demonstrated,[31-33] few high performance n-type semiconductors have been developed while molecular design strategies have led to a number of high performing ambipolar polymer semiconductors.[21] Using strategies described herein, there is no need for individual high performance p- or n-type systems; with the wide range of high mobility ambipolar polymers reported in the literature, the focus can be on matching energetics and selecting appropriate additives to function as traps.

REFERENCES

The following references are incorporated by reference herein:

[1] H. Sirringhaus, *Adv. Mater.* 2014, 26, 1319.
[2] S. Holliday, J. Donaghey, I. McCulloch, *Chem. Mater.* 2013, 26, 647.
[3] C. B. Nielsen, M. Turbiez, I. McCulloch, *Adv. Mater.* 2013, 25, 1859.
[4] D. Venkateshvaran, M. Nikolka, A. Sadhanala, V. Lemaur, M. Zelazny, M. Kepa, M. Hurhangee, A. J. Kronemeijer, V. Pecunia, I. Nasrallah, I. Romanov, K. Broch, I. McCulloch, D. Emin, Y. Olivier, J. Cornil, D. Beljonne, H. Sirringhaus, *Nature* 2014, 515, 384.
[5] H. R. Tseng, L. Ying, B. B. Y. Hsu, L. A. Perez, C. J. Takacs, G. C. Bazan, A. J. Heeger, *Nano Lett*, 2012, 12, 6353.
[6] R. S. Ashraf, I. Meager, M. Nikolka, M. Kirkus, M. Planells, B. C. Schroeder, S. Holliday, M. Hurhangee, C. B. Nielsen, H. Sirringhaus, I. McCulloch, *J. Am. Chem. Soc.* 2015, 137, 1314.
[7] D. M. de Leeuw, E. Cantatore, *Mater. Sci. Semicond. Process.* 2008, 11, 199.
[8] A. Facchetti, *Nat. Mater.* 2013, 12, 598.
[9] L. Dou, Y. Liu, Z. Hong, G. Li, Y. Yang, *Chem. Rev.* 2013, 115, 12633.
[10] H. N. Tsao, D. M. Cho, I. Park, M. R. Hansen, A. Mavrinskiy, D. Y. Yoon, R. Graf, W. Pisula, H. W. Spiess, K. Mullen, *J. Am. Chem. Soc.* 2011, 133, 2605.
[11] W. Zhang, J. Smith, S. E. Watkins, R. Gysel, M. McGehee, A. Salleo, J. Kirkpatrick, S. Ashraf, T. Anthopoulos, M. Heeney, I. McCulloch, *J. Am. Chem. Soc.* 2010, 132, 11437.
[12] B. Nketia-Yawson, H. Y. Lee, D. Seo, Y. Yoon, W. T. Park, K. Kwak, H. J. Son, B. Kim, Y. Y. Noh, *Adv. Mater.* 2015, 27, 3045.
[13] M. Wang, M. Ford, H. Phan, J. Coughlin, T.-Q. Nguyen, G. C. Bazan, *Chem. Commun.* 2016, 52, 3207.
[14] L.-L. Chua, J. Zaumseil, J.-F Chang, E. C.-W. Ou, P. K.-H. Ho, H. Sirringhaus, R. H. Friend, *Nature* 2005, 434, 194.
[15] Zamuseil, J., Sirringhaus, H. *Chem. Rev.* 2007, 107, 1296.
[16] X. Guo, M. Baumgarten, K. Muellen, *Prog. Polym. Sci.* 2013, 38, 1832.
[17] M. S. Kang, C. D. Frisbie, *ChemPhysChem.* 2013, 14, 1547.

[18] Y. Xu, H. Sun, E.-Y. Shin, Y.-F. Lin, W. Li, Y.-Y. Noh, *Adv. Mater.* 2016, 28, 8531.
[19] Nakano, M., Osaka, I., Takimiya, K., *Adv. Mater.* 2016, Published online.
[20] M. J. Ford, M. Wang, H. Phan, T.-Q. Nguyen, G. C. Bazan, *Adv. Funct. Mater.* 2016, 26, 4472.
[21] Y. Zhao, Y. Guo, Y. Liu, *Adv. Mater.* 2013, 25, 5372.
[22] Köhler, A., *Nat. Mater.* 2012, 11, 836.
[23] W. Li, K. H. Hendriks, W. S. C. Roelofs, Y. Kim, M. M. Wienk, R. A. J. Janssen, *Adv. Mater.* 2013, 25, 3182.
[24] M. Guide, J. D. A. Lin, C. M. Proctor, J. Chen, C. Garcia-Cervera, T.-Q. Nguyen, *J. Mater. Chem. A.* 2014, 2, 7890.
[25] Facchetti, A. *Mater. Today.* 2007, 10, 28.
[26] P. Docampo, S. Guldin, T. Leijtens, N. K. Noel, U. Steiner, H. J. Snaith, *Adv. Mater.* 2014, 26, 4013.
[27] G. Meller, T. Grasser, Organic Electronics, Springer, Hiedelberg, Baden-Württemberg, D E, 2010.
[28] K.-J. Baeg, D. Khim, J. W. Kim, Y.-Y. Noh, et al. *IEEE Electron Device Lett.* 2013, 34, 126.
[29] K.-J. Baeg, M. Caironi, Y.-Y. Noh, *Adv. Mater.* 2013, 25, 4210.
[30] L. Ying, B. B. Y. Hsu, H. Zhan, G. C. Welch, P. Zalar, L. A. Perez, E. J. Kramer, T.-Q. Nguyen, A. J. Heeger, W. Y. Wong, G. C. Bazan, *J. Am. Chem. Soc.* 2011, 133, 18538.
[31] T. N. Ng, D. E. Schwartz, P. Mei, B. Krusor, S. Kor, J. Veres, P. Broms, T. Eriksson, Y. Wang, O. Hagel, C. Karlsson, *Sci. Rep.* 2015, 5, 13457.
[32] S. P. Senanayak, V. K. Sangwan, J. J. McMorrow, K. Everaerts, Z. Chen, A. Facchetti, M. C. Hersam, T. J. Marks, K. S. Narayan, *Adv. Electron. Mater.* 2015, 1, 1500226
[33] M. Uno, Y. Kanaoka, B.-S. Cha, N. Isahaya, M. Sakai, H. Matsui, C. Mitsui, T. Okamoto, J. Takeya, T. Kato, M. Katayama, Y. Usami, T. Yamakami, *Adv. Electron. Mater.* 2015, 1, 1500178.
[34] Ford, M. et al. *Adv. Funct. Mater*. Vol. 26, Issue 25, Jul. 5, 2016, page 4616.
[35] Phan, H. et al. *Adv. Mater.,* 2015.
[36] Ying, L. et al. *J. Am. Chem. Soc.,* 2011.
[37] Gao, X. et al. *Pure Appl. Chem.,* 2008.
[38] http://www.ossila.com/products/spiro-ometad, Accessed Mar. 17, 2016.
[39] Li, W. et al. *Adv. Mater.,* 2013.
[40] Guide, M. et al. *J. Mater. Chem. A.,* 2014.
[41] Michael J. Ford, Ming Wang, Hung Phan, Thuc-Quyen Nguyen, Guillermo C. Bazan Fullerene Additives Convert Ambipolar Transport to p-Type Transport while Improving the Operational Stability of Organic Thin Film Transistors, by Michael J. Ford, Ming Wang, Hung Phan, Thuc-Quyen Nguyen, and Guillermo Bazan, Advanced Functional Materials, Volume 26, Issue 25, Jul. 5, 2016, Page 4616, including supplementary information.
[42] DiBenedetto et. al., Molecular Self-Assembled Monolayers and Multilayers for Organic and Unconventional Inorganic Thin-Film Transistor Applications, Adv. Mater. 2009, 21, 1407-1433 DOI 10.1002/adma.200803267.
[43] Carrier-Selective Traps: A New Approach for Fabricating Circuit Elements with Ambipolar Organic Semiconductors, Michael J. Ford, John G. Labram, Ming Wang, Hengbin Wang, Thuc-Quyen Nguyen, and Guillermo C. Bazan Advanced Electron. Mater. 2017 3, 1600537.

CONCLUSION

This concludes the description of the preferred embodiment of the present invention. The foregoing description of one or more embodiments of the invention has been presented for the purposes of illustration and description. It is not intended to be exhaustive or to limit the invention to the precise form disclosed. Many modifications and variations are possible in light of the above teaching. It is intended that the scope of the invention be limited not by this detailed description, but rather by the claims appended hereto.

What is claimed is:

1. A composition of matter, comprising:
   donor-acceptor copolymers each comprising a main chain section, the main chain section having a repeat unit that comprises a donor and an acceptor; and
   hole trapping compounds combined with the donor-acceptor copolymers so as to switch ambipolar transport of the donor-acceptor copolymers to unipolar n-type transport.

2. The composition of matter of claim 1, further comprising a solution comprising the hole trapping compounds and the donor-acceptor copolymers, wherein a total weight percentage (wt. %) of the hole trapping compounds in the solution is in a range of 0.005-50 wt. % based on a total weight of the solution.

3. The composition of matter of claim 2, wherein the wt. % is in a range of 0.005-10 wt. %.

4. The composition of matter of claim 1, further comprising a film cast from a solution, wherein:
   a total weight ($W_{CP}$) of the donor-acceptor copolymers added in the solution and a total weight $W_{HT}$ of the hole trapping compounds added in the solution are such that $[W_{CP}/(W_{CP}+W_{HT})] \times 100$ is in a range of 5%-99%.

5. The composition of matter of claim 1, wherein the hole trapping compounds each comprise at least one compound selected from Tetrathiafulvalene (TTF), a derivative of TTF, 1H-benzoimidazole (DMBI), a derivative of DMBI, Decamethylcobaltocene (DMC), a derivative of DMC, bicyclo [2,2,2]-octadiene-fused porphyrins, tetrabenzoporphyrin (BP or TBP), a derivative of BP, copper tetrabenzoporphyrin (CuBP), a derivative of CuBP, tetraethano-tetrabenzoporphyrin, a derivative of tetraethano-tetrabenzoporphyrin, copper tetraethano-tetrabenzoporphyrin, a derivative of copper tetraethano-tetrabenzoporphyrin, Spiro-MeOTAD, and a derivative of Spiro-MeOTAD.

6. The composition of matter of claim 5, wherein:
   the acceptor comprises a pyridine of the structure:

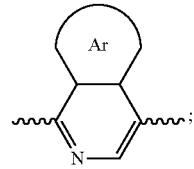

the donor comprises a dithiophene of the structure:

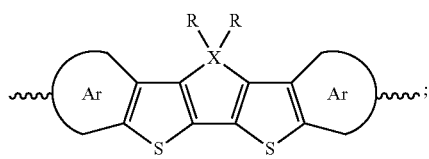

each R is independently hydrogen or a substituted or non-substituted alkyl, aryl, or alkoxy chain;
   X is C, Si, Ge, N or P;
   Ar is a substituted or non-substituted aromatic functional group or Ar is nothing and the valence of the pyridine ring is completed with hydrogen; and the pyridine is regioregularly arranged along the conjugated main chain section.

7. The composition of claim 1, wherein:
the acceptor comprises a fluorophenyl or fluorophenylene;
the donor comprises a dithiophene of the structure:

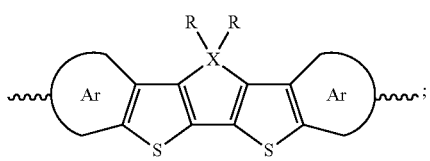

each R is independently hydrogen or a substituted or non-substituted alkyl, aryl, or alkoxy chain; and
X is C, Si, Ge, N or P.

8. The composition of matter of claim 1, wherein each of the donor-acceptor copolymers are:
poly[4-(4,4-dihexadecyl-4H-cyclopenta[1,2-b:5,4-b'] dithiophen-2yl)-alt-[1,2,5] thiadiazolo[3,4-c]pyridine] (PCDTPT), or
5 poly[5-fluoro-[2,1,3]benzothiadiazole-4,7-diyl(4,4-dihexadecyl-4H-cyclopenta[2,1-b:3,4-Y] dithiophene-2,6-diyl)-5-fluoro-[2,1,3]benzothiadiazole-7,4-diyl(4,4-dihexadecyl-4Hcyclopenta[2,1-b:3,4-b']dithiophene-2,6-diyl)] (PCDTFBT), or
a diketopyrrolopyrrole-thienothiophene copolymer DT-PDPP2T-TT.

9. A composition of matter, comprising:
a first region including:
donor-acceptor copolymers each comprising a main chain section, the main chain section having a repeat unit that comprises a donor and an acceptor; and
hole trapping compounds combined with the donor-acceptor copolymers so as to reduce hole current in the donor-acceptor copolymers; and
a second region, attached to the first region, including additional donor-acceptor copolymers combined with electron acceptor compounds, the electron acceptor compounds accepting electrons and reducing electron current in the additional donor-acceptor copolymers.

10. The composition of matter of claim 9, wherein the donor-acceptor copolymers in the first region and the additional donor-acceptor copolymers in the second region both comprise a backbone including the repeat unit including the donor and the acceptor.

11. The composition of matter of claim 1, wherein the donor-acceptor copolymers are regioregular.

12. A device comprising the composition of matter of claim 1, comprising:
an Organic Field Effect Transistor (OFET) comprising:
a source contact to the donor-acceptor copolymers;
a drain contact to the donor-acceptor copolymers;
a gate contact; and
a dielectric between the donor-acceptor copolymers and the gate contact.

13. The OFET of claim 12, wherein a hole current between the source and the drain contact is reduced by at least a factor of 100 with at most a factor of 10 reduction in electron current between the source and the drain contacts, as compared to the OFET comprising a film comprising the pristine donor-acceptor copolymers without the hole trapping compounds.

14. The device of claim 12, further comprising:
a second OFET comprising additional donor-acceptor copolymers combined with electron acceptor compounds, the electron acceptor compounds accepting electrons and reducing electron current in the additional donor-acceptor copolymers.

15. The device of claim 14, wherein:
a weight and composition of the hole trapping compounds,
a weight and composition of the donor-acceptor copolymers, and
a weight of and composition of the electron acceptor compounds,
are such that each of the OFETs have a mobility in a saturation regime of at least 1 cm$^2$ V$^{-1}$ s$^{-1}$ and an ON/OFF ratio of at least 1000.

16. A logic gate comprising the OFETs of claim 14.

17. The logic gate of claim 16, wherein the logic gate is an inverter.

18. The composition of matter of claim 1, wherein the hole trapping compounds have a HOMO level that is higher in energy (closer to vacuum) than the HOMO level of the donor-acceptor semiconducting copolymers.

19. The composition of matter of claim 18, wherein a first portion of the donor-acceptor semiconducting copolymers are p-type doped and a second portion of the donor-acceptor semiconducting copolymers are combined with electron acceptor compounds having a LUMO level lower than the LUMO level of the donor-acceptor semiconducting polymers.

20. The composition of matter of claim 1, wherein the ambipolar transport is switched so that the donor-acceptor copolymers comprise n-type donor-acceptor copolymers.

21. The composition of matter of claim 1, wherein the hole trapping compounds comprise isolating regions so that the hole trapping compound only accept holes and do not substantially transport the holes.

22. The OFET of claim 12, wherein the hole current is at most 10$^{-8}$ amps.

23. A composition of matter, comprising:
a film including:
donor-acceptor copolymers each comprising a main chain section, the main chain section having a repeat unit that comprises a donor and an acceptor; and
hole trapping compounds combined with the donor-acceptor copolymers so as to reduce hole current in the donor-acceptor copolymers, wherein:
the donor-acceptor copolymers and the hole trapping compounds are phase separated, and
the main chain axes of a plurality of the donor-acceptor copolymers are interconnected.

* * * * *